US009907822B2

(12) United States Patent
Tarleton et al.

(10) Patent No.: US 9,907,822 B2
(45) Date of Patent: Mar. 6, 2018

(54) THERAPEUTIC COMPOSITIONS AND METHODS FOR TREATING INFECTIONS

(71) Applicant: University of Georgia Research Foundation, Inc., Athens, GA (US)

(72) Inventors: Rick Tarleton, Bogart, GA (US); Samarchith Kurup, Iowa City, IA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/761,733

(22) PCT Filed: Jan. 17, 2014

(86) PCT No.: PCT/US2014/011967
§ 371 (c)(1),
(2) Date: Jul. 17, 2015

(87) PCT Pub. No.: WO2014/113625
PCT Pub. Date: Jul. 24, 2014

(65) Prior Publication Data
US 2015/0352160 A1 Dec. 10, 2015

Related U.S. Application Data

(60) Provisional application No. 61/754,127, filed on Jan. 18, 2013.

(51) Int. Cl.

| | |
|---|---|
| ***A61K 48/00*** | (2006.01) |
| ***A61K 35/68*** | (2006.01) |
| ***C12N 5/09*** | (2010.01) |
| ***C12N 1/10*** | (2006.01) |
| ***A61K 35/13*** | (2015.01) |
| ***A61K 35/66*** | (2015.01) |
| ***A61K 35/76*** | (2015.01) |
| ***C07K 14/22*** | (2006.01) |
| ***C07K 14/255*** | (2006.01) |

(52) U.S. Cl.
CPC .............. *A61K 35/68* (2013.01); *A61K 35/13* (2013.01); *A61K 35/66* (2013.01); *A61K 35/76* (2013.01); *C07K 14/22* (2013.01); *C07K 14/255* (2013.01); *C12N 1/10* (2013.01); *C12N 5/0693* (2013.01)

(58) Field of Classification Search
None
See application file for complete search history.

(56) References Cited

U.S. PATENT DOCUMENTS

2003/0175287 A1* 9/2003 Medzhitov ........... A61K 39/385
424/185.1

FOREIGN PATENT DOCUMENTS

WO WO 2011/097573 A2 8/2011
WO WO 2014/113625 A1 7/2014

OTHER PUBLICATIONS

Kajikawa et al. Vaccine 2010;3409-15.*
Garaude et al. Oncotarget 2012;3:361-2.*
Junqueira et al. PNAS 2011;108:19695-700.*
Hobohm et al. Cri Rev Immunol 2008;28:95-107.*
Garaude et al. Sci Translation Med Feb. 2012;4-120ra:1-11.*
Kajikawa et al. Vaccine 2007;3409-15.*
Paiva et al. Exp Parasitol 1999;91:7-19.*
Turner et al. Infect Immunity 2001;69:4969-79.*
International Patent Application No. PCT/US2014/011967, filed Jan. 17, 2014; International Search Report and Written Opinion dated Apr. 15, 2014; 10 pages.
International Patent Application No. PCT/US2014/011967, filed Jan. 17, 2014; International Preliminary Report on Patentability dated Jul. 21, 2015; 10 pages.
Tarleton, Rick L. "Transmission-Blocking Live Vaccine for Chagas Disease" Grant Abstract, Grant No. AI089952 [online]. National Institutes of Health, project dates Dec. 1, 2011 to Nov. 30, 2016 [retrieved on Jun. 29, 2016]. Retrieved from the Internet: <URL:projectreporter.nih.gov/project_info_details.cfm?icde=0&aid=8390470; 2 pgs.
Adachi et al., "Targeted disruption of the MyD88 gene results in loss of IL-1- and IL-18-mediated function" Immunity, 1998; 9(1):143-50.
Agrawal et al., "Genetic evidence that an endosymbiont-derived endoplasmic reticulum-associated protein degradation (ERAD) system functions in import of apicoplast proteins" J Biol Chem, 2009; 284:33683-91. Available online Oct. 6, 2009.
Ahrens et al., "F-actin is an evolutionarily conserved damage-associated molecular pattern recognized by DNGR-1, a receptor for dead cells" Immunity, 2012; 36:635-45.
Akira et al., "Toll-like receptors: critical proteins linking innate and acquired immunity" Nat Immunol, Aug. 2001; 2(8):675-80.
Almeida et al., "Proinflammatory activity of glycosylphosphatidylinositol anchors derived from Trypanosoma cruzi: structural and functional analyses" J Leukoc Biol, Oct. 2001; 70(4):467-77.
Amigorena et al., "Intracellular mechanisms of antigen cross presentation in dendritic cells" Curr Opin Immunol, Feb. 2010; 22(1):109-17.
Andersen-Nissen et al., "Evasion of Toll-like receptor 5 by flagellated bacteria" Proc Natl Acad Sci USA, 2005; 102:9247-52.
Bafica et al., "Cutting edge: TLR9 and TLR2 signaling together account for MyD88-dependent control of parasitemia in Trypanosoma cruzi infection" J Immunol, 2006; 177:3515-9.
Bengsch et al., "Analysis of CD127 and KLRG1 expression on hepatitis C virus-specific CD8+ T cells reveals the existence of different memory T-cell subsets in the peripheral blood and liver" J Virol, 2007; 81:945-53.

(Continued)

*Primary Examiner* — Janice Li
(74) *Attorney, Agent, or Firm* — Mueting, Raasch & Gebhardt, P.A.

(57) ABSTRACT

This disclosure describes, in one aspect, a composition that includes a transgenic pathogen that expresses a heterologous pathogen associated molecular pattern (PAMP). In some embodiments, the pathogen may be attenuated. In some embodiments, the pathogen can include *T. cruzi*. In another aspect, this disclosure describes a method of treating an infection in a subject. Generally, the method includes administering to the subject, in an amount effective to treat the infection, a pathogen genetically modified to express a pathogen-associated molecular pattern (PAMP) not natively expressed by the pathogen.

8 Claims, 17 Drawing Sheets

(56) References Cited

OTHER PUBLICATIONS

Berg et al., "Contribution of CD8+ T cells to innate immunity: IFN-gamma secretion induced by IL-12 and IL-18" Eur J Immunol, 2002; 32:2807-16.
Bocek et al., "Interferon gamma enhances both in vitro and in vivo priming of CD4+ T cells for IL-4 production" J Exp Med, 2004; 199:1619-30.
Bustamante et al., "Drug-induced cure drives conversion to a stable and protective CD8+ T central memory response in chronic Chagas disease" Nat Med, 2008; 14: 542-50.
Campos et al., "Activation of Toll-like receptor-2 by glycosylphosphatidylinositol anchors from a protozoan parasite" J Immunol, 2001; 167:416-23.
Coats et al., "Antagonistic lipopolysaccharides block *E. coli* lipopolysaccharide function at human TLR4 via interaction with the human MD-2 lipopolysaccharide binding site" Cell Microbiol, 2007; 9:1191-1202.
Coffman et al., "Vaccine adjuvants: putting innate immunity to work" Immunity, 2010; 33:492-503.
Costales et al., "Cytokine-dependent and independent gene expression changes and cell cycle block revealed in Trypanosoma cruzi-infected host cells by comparative mRNA profiling" BMC Genomics, 2009; 10:252.
Cui et al., "Effects of Signal 3 during CD8 T cell priming: Bystander production of IL-12 enhances effector T cell expansion but promotes terminal differentiation" Vaccine, 2009; 27:2177-87.
Cummings et al., "Rapid quantitation of Trypanosoma cruzi in host tissue by real-time PCR" Mol Biochem Parasitol, Jun. 2003; 129(1):53-9.
Doughty, "Pathogen Associated Molecular Patterns, Pattern Recognition Receptors and Pediatric Sepsis" The Open Inflammation Journal, 2011; 4(Suppl 1-M5):31-48.
Fearon et al., "The instructive role of innate immunity in the acquired immune response" Science, Apr. 5, 1996; 272(5258):50-3.
Fralish et al., "Genetic immunization with LYT1 or a pool of trans-sialidase genes protects mice from lethal Trypanosoma cruzi infection" Vaccine, Jun. 20, 2003; 21(21-22):3070-80.
Garg et al., "Delivery by Trypanosoma cruzi of proteins into the MHC class I antigen processing and presentation pathway" J Immunol, Apr. 1, 1997; 158(7):3293-302.
Gupta et al., "Prophylactic efficacy of TcVac2 against Trypanosoma cruzi in mice" PLoS Negl Trop Dis, 2010; 4: e797.
Hayashi et al., "The innate immune response to bacterial flagellin is mediated by Toll-like receptor 5" Nature, Apr. 26, 2001; 410(6832):1099-103.
Ibegbu et al., "Expression of killer cell lectin-like receptor G1 on antigen-specific human CD8+ T lymphocytes during active, latent, and resolved infection and its relation with CD57" J Immunol, 2005; 174:6088-94.
Iwasaki et al., "Toll-like receptor control of the adaptive immune responses" Nat Immunol, Oct. 2004; 5(10):987-95.
Iwasaki et al., "Regulation of adaptive immunity by the innate immune system" Science, 2010; 327:291-5.
Kadowaki et al., "Natural interferon alpha/beta-producing cells link innate and adaptive immunity" J Exp Med, 2000; 192:219-26.
Kang et al., "MyD88 plays an essential role in inducing B cells capable of differentiating into antibody-secreting cells after vaccination" J Virol, 2011; 85:11391-400.
Koenen et al., "The inflammasomes and caspase-1 activation: a new mechanism underlying increased inflammatory activity in human visceral adipose tissue" Endocrinology, 2011; 152:3769-78.
Kriegel et al., Dual TNF-[alpha]/Cyclin D1 Gene Silencing With an Oral Polymeric Microparticle System as a Novel Strategy for the Treatment of Inflammatory Bowel Disease. Clin Trans Gastroenterol, 2011; 2: e2.
Kurup et al., "Enhancing Immunity to Trypanosoma Cruzi by Heterologous Expression of TLR Ligands" <astmh.org> 2011; p. 161. Provided with the International Search Report for PCT/US2014/011967 dated Apr. 15, 2014.
Kurup et al., "Perpetual Expression of PAMPs Necessary for Optimal Immune Control and Clearance of a Persitent Pathogen" Nature Communications, Oct. 23, 2013; 4:2616. 10 pages.
Lorenzi et al., "Integration of expression vectors into the ribosomal locus of Trypanosoma cruzi" Gene, May 22, 2003; 310:91-9.
Martin et al., "Antigen-specific T cells maintain an effector memory phenotype during persistent Trypanosoma cruzi infection" J Immunol, 2005; 174, 1594-1601.
Martin et al., "CD8+ T-Cell responses to Trypanosoma cruzi are highly focused on strain-variant trans-sialidase epitopes" PLoS Pathog, 2006; 2:e77.
Massari et al., "Cutting edge: Immune stimulation by neisserial porins is toll-like receptor 2 and MyD88 dependent" J Immunol, 2002; 168:1533-7.
Mayer et al., "The functional heterogeneity of type 1 effector T cells in response to infection is related to the potential for IFN-gamma production" J Immunol, 2005; 174:7732-9.
Medzhitov et al., "A human homologue of the *Drosophila* Toll protein signals activation of adaptive immunity" Nature, Jul. 24, 1997; 388(6640):394-7.
Mescher et al., "Signals required for programming effector and memory development by CD8+ T cells" Immunol Rev, Jun. 2006; 211:81-92.
Miao et al., "Cytoplasmic flagellin activates caspase-1 and secretion of interleukin 1beta via Ipaf" Nat Immunol, Jun. 2006; 7(6):569-75.
Miao et al., "TLR5 and Ipaf: dual sensors of bacterial flagellin in the innate immune system" Semin Immunopathol, Sep. 2007; 29(3):275-88.
Montminy et al., "Virulence factors of Yersinia pestis are overcome by a strong lipopolysaccharide response" Nat Immunol, Oct. 2006; 7(10):1066-73.
Napolitani et al., "Selected Toll-like receptor agonist combinations synergistically trigger a T helper type 1-polarizing program in dendritic cells" Nat Immunol, 2005; 6:769-76.
Oliveira et al., "Impaired innate immunity in Tlr4(-/-) mice but preserved CD8+ T cell responses against Trypanosoma cruzi in Tlr4-, Tlr2-, Tlr9- or Myd88-deficient mice" PLoS Pathog, 2010; 6:e1000870.
Ouaissi et al., "The Trypanosoma cruzi Tc52-released protein induces human dendritic cell maturation, signals via Toll-like receptor 2, and confers protection against lethal infection" J Immunol, 2002; 168:6366-74.
Padilla et al., "CD8+ T cells in Trypanosoma cruzi infection" Curr Opin Immunol, 2009a; 21:385-90.
Padilla et al., "Insufficient TLR activation contributes to the slow development of CD8+ T cell responses in Trypanosoma cruzi infection" J Immunol, 2009b; 183:1245-52.
Pasare et al., "Toll pathway-dependent blockade of CD4+CD25+ T cell-mediated suppression by dendritic cells" Science, Feb. 14, 2003; 299(5609):1033-6.
Pasare et al., "Toll-like receptors and acquired immunity" Semin Immunol, Feb. 2004; 16(1):23-6.
Pasare et al., "Toll-like receptors: linking innate and adaptive immunity" Adv Exp Med Biol, 2005; 560:11-8.
Phythian-Adams et al., "CD11c depletion severely disrupts Th2 induction and development in vivo" J Exp Med, 2010; 207, 2089-96.
Poyet et al., "Identification of Ipaf, a human caspase-1-activating protein related to Apaf-1" J Biol Chem, 2001; 276:28309-13.
Pulendran, "Modulating vaccine responses with dendritic cells and Toll-like receptors" Immunol Rev, Jun. 2004; 199:227-50.
Querec et al., "Yellow fever vaccine YF-17D activates multiple dendritic cell subsets via TLR2, 7, 8, and 9 to stimulate polyvalent immunity" J Exp Med, 2006; 203:413-24.
Reife et al., "Porphyromonas gingivalis lipopolysaccharide lipid A heterogeneity: differential activities of tetra- and penta-acylated lipid A structures on E-selectin expression and TLR4 recognition" Cell Microbiol, 2006; 8:857-68.
Reinhardt et al., "Visualization of IL-12/23p40 in vivo reveals immunostimulatory dendritic cell migrants that promote Th1 differentiation" J Immunol, 2006; 177:1618-27.
Schnare et al., "Toll-like receptors control activation of adaptive immune responses" Nat Immunol, Oct. 2001; 2(10):947-50.

(56) References Cited

OTHER PUBLICATIONS

Singleton et al., "Neisserial porin-induced dendritic cell activation is MyD88 and TLR2 dependent" J Immunol, 2005; 174:3545-50.

Stetson et al., "Constitutive cytokine mRNAs mark natural killer (NK) and NK T cells poised for rapid effector function" J Exp Med, 2003; 198:1069-76.

Takeda et al., "TLR signaling pathways" Semin Immunol, Feb. 2004; 16(1):3-9.

Tarleton, "Depletion of CD8+ T cells increases susceptibility and reverses vaccine-induced immunity in mice infected with Trypanosoma cruzi" J Immunol, Jan. 15, 1990; 144(2):717-24.

Tarleton et al., "Difficult diagnosis of the fragile X syndrome made possible by direct detection of DNA mutations" J Med Genet, 1992; 29:726-9.

Tarleton, "Immune system recognition of Trypanosoma cruzi" Curr Opin Immunol, Aug. 2007; 19(4):430-4.

Theiner et al., "TLR9 cooperates with TLR4 to increase IL-12 release by murine dendritic cells" Mol Immunol, Jan. 2008; 45(1):244-52.

Trinchieri, "Interleukin-12 and the regulation of innate resistance and adaptive immunity" Nat Rev Immunol, Feb. 2003; 3(2):133-46.

Turley et al., "The stromal and haematopoietic antigen-presenting cells that reside in secondary lymphoid organs" Nat Rev Immunol, Dec. 2010; 10(12):813-25.

Voehringer et al., "Lack of proliferative capacity of human effector and memory T cells expressing killer cell lectinlike receptor G1 (KLRG1)" Blood, 2002; 100:3698-702.

Wolfgang et al., "Pseudomonas aeruginosa regulates flagellin expression as part of a global response to airway fluid from cystic fibrosis patients" Proc Natl Acad Sci USA, 2004; 101:6664-8.

Zhang et al., "The dendritic cell receptor Clec9A binds damaged cells via exposed actin filaments" Immunity, 2012; 36:646-57.

* cited by examiner

THERAPEUTIC COMPOSITIONS AND METHODS FOR TREATING INFECTIONS

CROSS-REFERENCE TO RELATED APPLICATION

This application is the § 371 U.S. National Stage of International Application No. PCT/US14/11967, filed 17 Jan. 2014, which claims priority to U.S. Provisional Patent Application Ser. No. 61/754,127, filed Jan. 18, 2013, each of which is incorporated herein by reference in its entirety.

GOVERNMENT FUNDING

The present invention was made with government support under Grant No. AI44979 and Grant No. AI089952, each of which was awarded by The National Institutes of Health. The Government has certain rights in this invention.

SUMMARY

This disclosure describes, in one aspect, a composition that includes a transgenic pathogen that expresses a heterologous pathogen associated molecular pattern (PAMP) or associated molecular patterns (DAMP). In some embodiments, the pathogen may be attenuated. In some embodiments, the PAMP can include an agonist of at least one Toll-Like Receptor (TLR) such as, for example, TLR 1, TLR 2, or TLR 5. In some embodiments, PAMP can include an agonist of at least one intracellular pattern recognition receptor (PRR) such as, for example, Neuronal Apoptosis Inhibitory Protein 5/IL-1β-converting enzyme protease-activating factor (NAIP5/Ipaf).

In another aspect, this disclosure describes a method of treating an infection in a subject. Generally, the method includes administering to the subject, in an amount effective to treat the infection, a pathogen genetically modified to express a pathogen-associated molecular pattern (PAMP) not natively expressed by the pathogen. In some embodiments, the pathogen can include a virus, a bacterium, or a protozoan. In some embodiments, the protozoan can include *T. cruzi*. In some embodiments, the pathogen may be attenuated.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
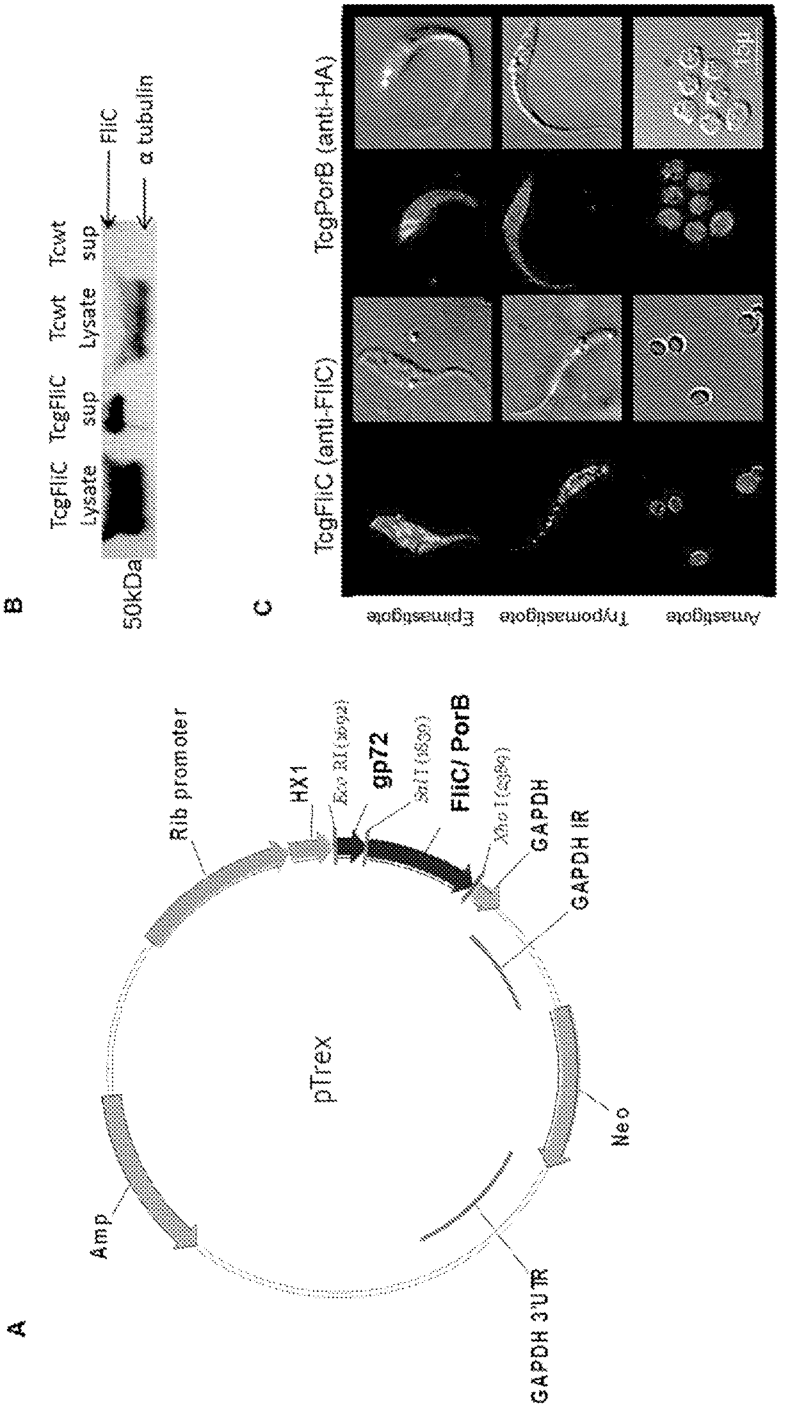
FIG. 1. PAMP transgenic *T. cruzi* secretes the PAMPs and presents it in all life cycle stages. (A) *S. typhimurium* flagellin (FliC) or *N. meningitidis* porin (PorB) cloned in pTREX expression vector with gp72 signal sequence at their 5' end to make transgenic *T. cruzi* secreting FliC (TcgFliC) or PorB (TcgPorB) (B) TcgFliC or Tcwt trypomastigote stage lysate and culture supernatant immunoblotted with antibodies against FliC or α-tubulin. (C) FliC or PorB expression in the epimastigote, trypomastigote, and amastigote stages of TcgFliC or TcgPorB respectively determined by indirect immunofluorescence/DIC microscopy, modifying the protocol described in the Examples. Anti-FliC or anti-HA antibodies were used to mark the target proteins.

This disclosure describes compositions and methods useful for treating infections by, for example, bacteria, viruses, and parasites. One can genetically modify a pathogen such as, for example, the human parasite *T. cruzi* to express one or more pathogen associated molecular patterns (PAMPs) that are not natively expressed by the pathogen. PAMPs are involved in both innate immunity and adaptive immunity. Administering a pathogen genetically modified to express one or more PAMPs can augment the subject's native immune response to the infection. As a result, administering the genetically modified pathogen as described herein can result in a reduction of the duration, extent, and/or severity of the infection. Moreover, if one selects a pathogen such as *T. cruzi* that can persist in the subject after administration, the beneficial effects of the PAMP expression by the pathogen can similarly persist for a period greater than by, for example, simply providing free PAMPs as an adjuvant component in a vaccination or other medicament.

As used herein, the term "treat" or variations thereof refer to reducing, limiting progression, ameliorating, or resolving, to any extent, the symptoms or clinical signs related to a condition. As used herein, "ameliorate" and variations thereof refer to any reduction in the extent, severity, frequency, and/or likelihood of a symptom or clinical sign characteristic of a particular condition. "Symptom" refers to any subjective evidence of disease or of a patient's condition. "Sign" or "clinical sign" refers to an objective physical finding relating to a particular condition capable of being found by one other than the patient.

In the description that follows, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

Pathogen associated molecular patterns (PAMPs) are known to be involved in initiating innate immune responses and to inducing and directing subsequent adaptive immunity. PAMPs are effective indicators of the presence of particular pathogens, in part, because certain PAMPs can be unique to certain classes of pathogens. Also, certain PAMPs can be required for pathogen survival and thus cannot be easily altered, suppressed, or hidden by a pathogen. Thus, most of the studies that established the role of PAMPs in inducing and directing innate or adaptive immune responses are based on negating the ability of the host to respond to these molecular patterns rather than by blocking PAMP expression.

We use the protozoan *Trypanosoma cruzi* as a model pathogen to evaluate the role of PAMPs in influencing adaptive immunity at and beyond its onset. As used herein, the term "pathogen" refers to any conventional infectious pathogen (e.g., a bacterium, a virus, a fungus, a protozoan, a helminth, etc.) but also includes non-infectious cells such as, for example, tumor cells. Thus, a pathogen may be acellular, unicellular, or multicellular. While described below in the context of an exemplary embodiment in which the pathogen is *T. cruzi*, the compositions and methods described herein can be made and/or practiced using any pathogen. Exemplary alternative pathogens include, for example, infectious pathogens such as, for example, a bacterium, a virus, a fungus, a protozoan, or a helminth, as well as non-infectious pathogens such as, for example, tumor cells.

*T. cruzi* is the etiological agent of Chagas disease, a prevalent human parasitic disease in the Americas. *T. cruzi* trypomastigotes stimulate a very weak host cell response during invasion and elicit significantly delayed adaptive immune responses, strongly suggesting the relative absence of potent PAMPs on live, invading parasites. Although several endogenous PAMPs have been identified in *T. cruzi*, their failure to impact the strength of adaptive immune responses suggests that the putative PAMPs are not readily available on live *T. cruzi* and have little relevance to anti-*T. cruzi* immunity.

Specifically, we generate transgenic *T. cruzi* expressing potent exogenous (non-*T. cruzi*, bacteria-derived) protein PAMPs and show that this expression induces superior innate immune responses and drives more rapid and persistently stronger adaptive immunity in mice. Expression of bacterial PAMPs by transgenic *T. cruzi* resulted in enhanced innate immune responses and a more robust *T. cruzi*-specific $CD8^+$ T cell response, with increased IFNγ- and TNFα-producing $CD4^+$ and $CD8^+$ T cells. Co-inoculating PAMPs with *T. cruzi* or temporarily anchoring exogenous PAMPs on *T. cruzi* can enhance the early adaptive immune response. Our transgenic *T. cruzi* that can continuously express PAMPs, however, were able to sustain this enhanced response and thus promote better control of the infection. *T. cruzi* transgenic for bacterial PAMP expression also boost *T. cruzi*-specific immune responses in mice chronically infected with wild-type *T. cruzi* and reduce parasite load in these mice, thus demonstrating their potential as therapeutic vaccines. These findings further support the relevance of PAMPs, particularly in persistent infections, and may also be applicable for improving live-attenuated vaccines.

PAMP Transgenesis in *T. cruzi* Enhances Innate Immune Responses

We chose to express protein PAMPs in *T. cruzi* since PAMP expression can be stably generated by transgenesis of a single coding region. In contrast, polysaccharides or nucleic acid PAMPs require transferring an entire biosynthetic pathways into *T. cruzi*. Coding regions encoding the *Salmonella typhimurium* flagellin (fliC) and *Neisseria meningitidis* porin (porB) were amplified by PCR and cloned into the pTREX plasmid (Lorenzi et al., 2003. *Gene* 310: 91-99) with a *T. cruzi* secretory signal peptide from gp72 (Garg et al., 1997. *J Immunol* 158:3293-3302) at their 5' end (FIG. 1A). *S. typhimurium* FliC is a ligand for both TLR 5 and Neuronal Apoptosis Inhibitory Protein (NAIP)5/IL-1β-converting enzyme protease-activating factor (Ipaf). *Neisseria meningitidis* PorB is a ligand for TLR 1/2. PAMP-transgenic *T. cruzi* expressing FliC (TcgFliC) or PorB (TcgPorB) were engineered by transfecting these constructs into wild-type (WT), Brazil strain *T. cruzi* (Tcwt). The signal peptide ensured secretion (FIG. 1B) of the protein PAMPs expressed by the PAMP-transgenic *T. cruzi* in epimastigote, trypomastigote, and amastigote life stages (FIG. 1C).

Figure 2:
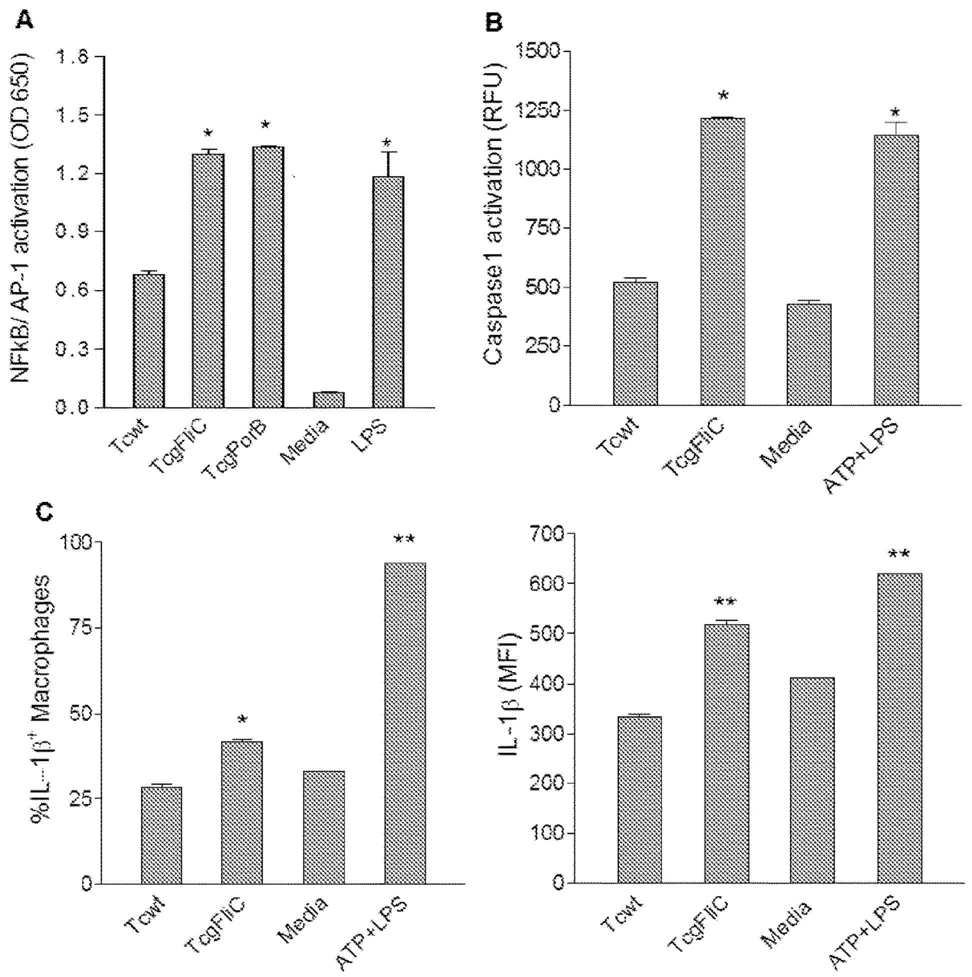
FIG. 2. PAMP transgenesis in *T. cruzi* enhances cellular innate immune responses (A) NFkB/AP-1 activation in reporter cells incubated with wild-type *T. cruzi* (Tcwt), or PAMP transgenic *T. cruzi* (TcgFliC or TcgPorB) trypomastigotes for 12 hours. Media or *E. coli*-derived LPS were used as negative and positive controls, respectively. (B) Caspasel activation in (TLR $5^-$) macrophages incubated with Tcwt or TcgFliC trypomastigotes for 12 hours. Media or ATP with *E. coli*-derived LPS served as negative and positive controls, respectively. (C) The proportion of (TLR $5^-$) macrophages producing IL-1β on incubation with Tcwt or TcgFliC trypomastigotes for 18 hours. Media or ATP with *E. coli*-derived LPS served as negative and positive controls, respectively. (D) IL-1β mean fluorescence intensity (MFI) per cell by TLR $5^-$ macrophages incubated with Tcwt or TcgFliC trypomastigotes for 18 hours. Media or ATP with *E. coli*-derived LPS served as negative and positive controls, respectively. All data show mean±SEM and are representative of at least three separate experiments. * indicates $p \leq 0.05$, ** indicates $p \leq 0.01$, in each case as determined by student t-test comparing the indicated groups to Tcwt.
Figure 3:
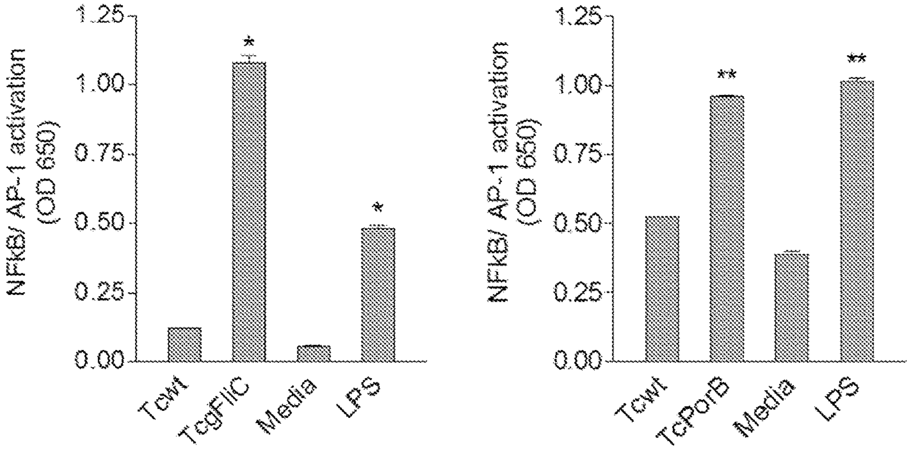
FIG. 3. PAMP transgenesis in *T. cruzi* enhances the innate immune responses. NFkB/AP-1 activation in reporter cells incubated with epimastigote stage lysates of Tcwt, TcgFliC or TcgPorB for 18 hours. Media or *E. coli*-derived LPS served as negative and positive controls, respectively. Data represented as mean±SEM from one of three separate experiments. * indicates $p \leq 0.05$, ** indicates $p \leq 0.01$, in each case as determined by student t-test comparing the indicated groups to Tcwt.

Stimulation of TLRs 1/2 or TLR 5 ultimately activates the transcription factors NFkB/AP-1 and promotes immunity at least in part by inducing the production of inflammatory cytokines NFkB/AP-1 reporter cell lines exhibited significantly increased NFkB/AP-1 activation by TcgFliC or TcgPorB live trypomastigotes (FIG. 2A) or epimastigote lysates (FIG. 3) relative to wild-type *T. cruzi* parasites (Tcwt). FliC is also an NAIP5/ipaf ligand that induces IL-1β production in antigen presenting cells (APCs). FliC-expressing *T. cruzi* potentiated strong caspasel activation (FIG. 2B) and production of IL1β in TLR 5-deficient macrophages (FIGS. 2C and 2D), demonstrating that *T. cruzi*-expressed FliC exhibits both of the PAMP properties of *Salmonella* flagellin.

Figure 4:
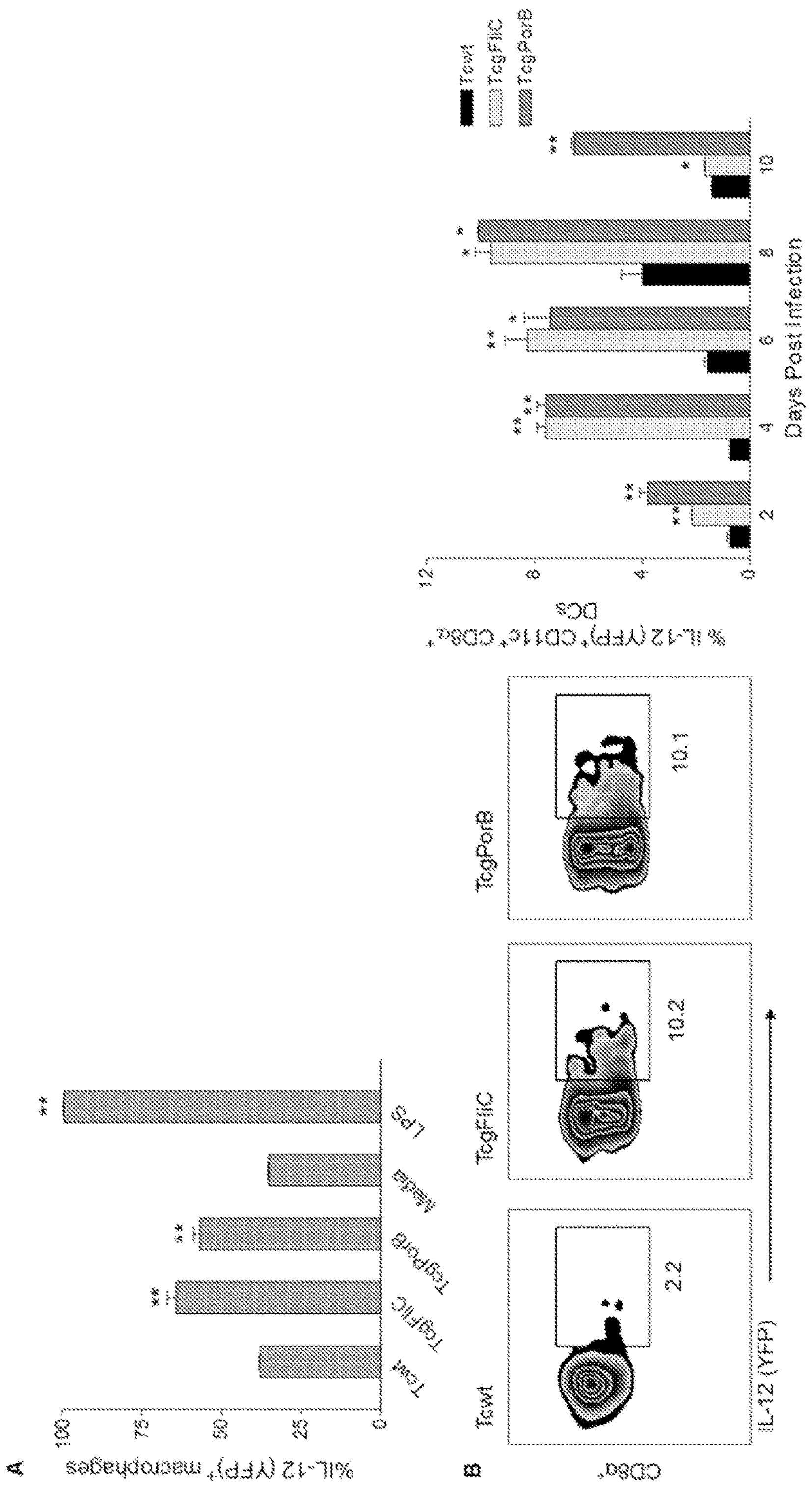
FIG. 4. PAMP transgenic *T. cruzi* induces higher frequencies of IL-12 producing APCs (A) The proportion of peritoneal exudate macrophages with induced IL-12 (YFP) on incubation with Tcwt, TcgFliC or TcgPorB trypomastigotes for 18 hours. Media or *E. coli*-derived LPS served as negative and positive controls, respectively. Data presented as mean±SEM and are representative of three separate experiments. (B) IL-12 producing ($CD11c^+$ $CD8\alpha^+$) cDC recruitment into the draining lymph nodes on Tcwt, TcgFliC or TcgPorB infection of IL-12yet40 mice. Flow plots show representative data from six days post-inoculation, with the numbers inset indicating the percentage of IL-12 producing cDCs. (C) Kinetics of $IL\text{-}12^+$ ($CD11c^+$ $CD8\alpha^+$) cDC recruitment. Data are represented as mean±SEM from one of 3 separate experiments, with at least 3 mice/group. * indicates $p \leq 0.05$, ** indicates $p \leq 0.01$, in each case as determined by student t-test comparing the indicated groups to Tcwt (A), at the corresponding time points (B).
Figure 5:
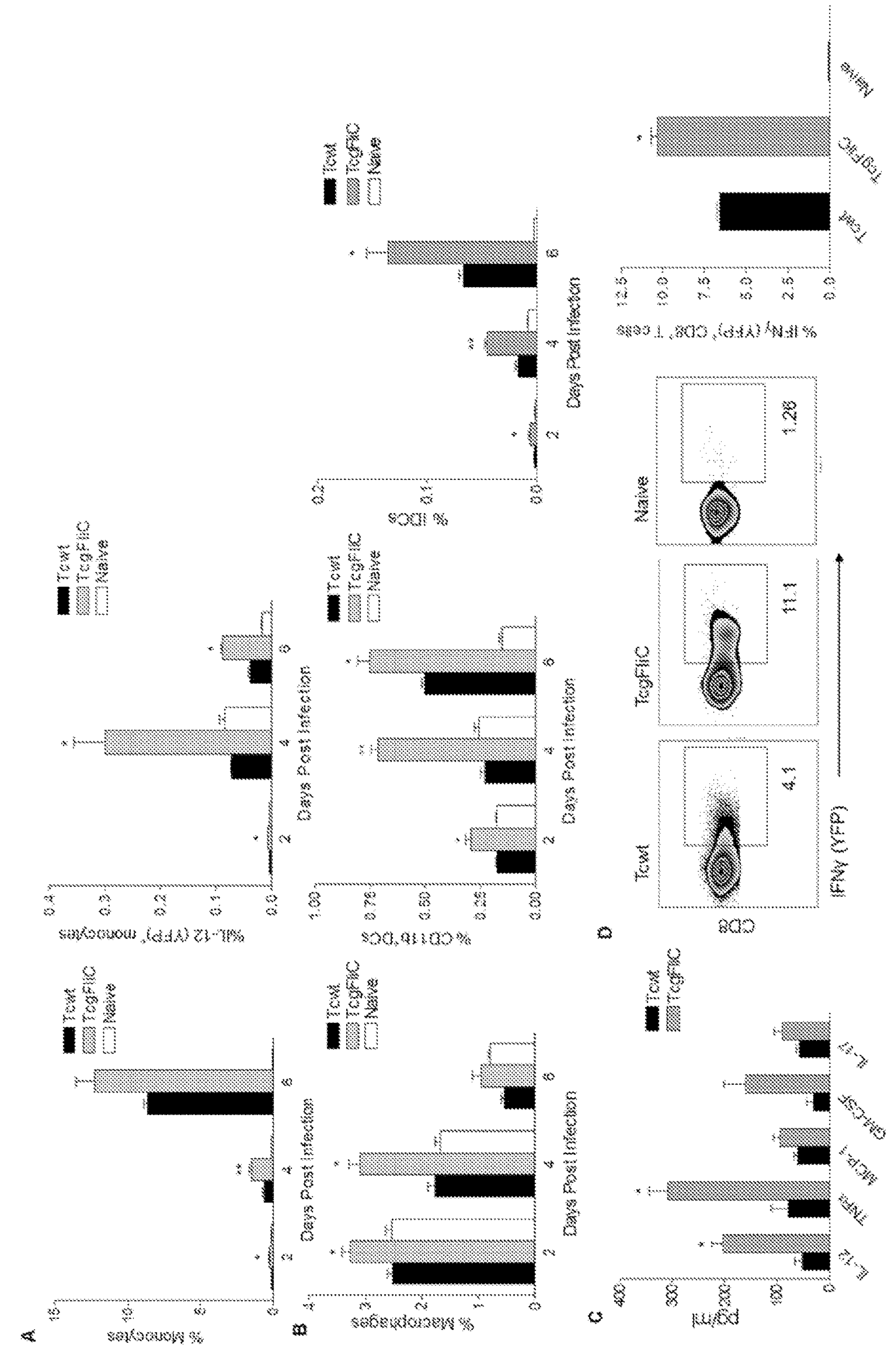
FIG. 5. PAMP transgenesis in *T. cruzi* enhances systemic innate immune responses in vivo. (A) The proportion of blood derived monocytes and their IL-12 producing subset at the site (s.c) of Tcwt or TcgFliC infection in IL-12yet40 mice at various time points post infection. Nave mice were inoculated with media alone. (B) The proportion of resident macrophages, $CD11b^+$ DCs, or iDCs at the site of Tcwt or TcgFliC infection in IL-12yet40 mice at various time points post infection. Nave mice were inoculated with media alone. (C) Serum levels of various cytokines in C57B1/6 mice infected with Tcwt or TcgFliC, four days post-inoculation. (D) Percentage of $CD8^+$ T cells producing IFNγ in the draining lymph nodes with Tcwt or TcgFliC infected (f.p) Yeti mice, six days post-inoculation. Representative flow plots with the numbers inset indicating the percentage of IFNγ producing $CD8^+$ T cells. In the right panel, data represented as mean±SEM from one of three separate experiments with 3-6 mice/group. * indicates $p \leq 0.05$, ** indicates $p \leq 0.01$, in each case as determined by student t-test comparing the indicated groups to Tcwt (C and D), at the corresponding time points (A and B).

The innate immune response-inducing activity of PAMP-transgenic *T. cruzi* trypomastigotes was also evident in IL-12yet40 reporter mice in which cells expressing IL-12/IL-23 p40 subunit also express yellow fluorescent protein (YFP). Peritoneal exudate macrophages exposed in vitro to PAMP-transgenic *T. cruzi* produced IL-12 at an increased frequency relative to those exposed to wild-type *T. cruzi* (FIG. 4A). Additionally, TcgFliC and TcgPorB infections of IL-12yet40 reporter mice resulted in a more rapid and increased infiltration of the IL-12-producing $CD11c^+$ $CD8\alpha^+$ classical dendritic cells (cDCs) into the draining lymph nodes (FIGS. 4B and 4C). TcgFliC infection also altered the lineage bias of the inflammatory cells infiltrating or prevailing at the site of infection, with increased numbers of blood-derived monocytes ($CD45^+CD11b^+CD11c^-Gr\text{-}1^{int}$), macrophages ($CD45^+CD11b^+CD11c^-F4/80^+$), inflammatory DCs ($CD45^+CD11b^+CD11c^{hi}Gr\text{-}1^{int}$), and other non-classical ($CD45^+CD11b^+CD11c^+CD8\alpha^-$) DCs, as compared to wild-type *T. cruzi* infection (FIGS. 5A and 5B). Classical ($CD45^+CD11b^-CD11c^+CD8\alpha^+$) DCs remained undetectable at the site of infection in either case. TcgFliC infection was also associated with enhanced recruitment of IL-12-producing monocytes (FIG. 5A) and neutrophils ($CD45^+CD11b^+Gr\text{-}1^{hi}$) to the site of infection. The innate immune enhancing effect of PAMP transgenesis was also evident systemically with significantly higher serum levels of IL-12 and TNFα compared to Tcwt infection (FIG. 5C).

IFNγ produced by naïve $CD8^+$ T cells in a T cell receptor (TCR)-independent, IL-12-mediated manner early in the infection appears to be involved in the initial immune responses to a number of pathogens. To measure the IFNγ induced early in response to *T. cruzi* infection, we used the IFNγ reporter (Yeti) mice, wherein cells expressing IFNγ concurrently express enhanced-yellow fluorescent protein (eYFP) (Mayer et al., 2005. *J Immunol* 174:7732-7739; Stetson et al., 2003. *J Exp Med* 198:1069-1076). We observed significantly higher proportions of $IFN\gamma^+CD8^+$ T cells (but undetectable *T. cruzi*-specific ($TSKb20^+$) $CD8^+$ T cells (not shown)) in the draining lymph nodes with TcgFliC infection compared to infection with wild-type *T. cruzi*, Tcwt (FIG. 5D). Taken together, these results indicate that the expression of bacterial PAMPs in *T. cruzi* markedly enhances innate immune activation both in vitro and in vivo.

PAMP Transgenesis in *T. cruzi* Enhances Adaptive Immune Responses

Figure 6:
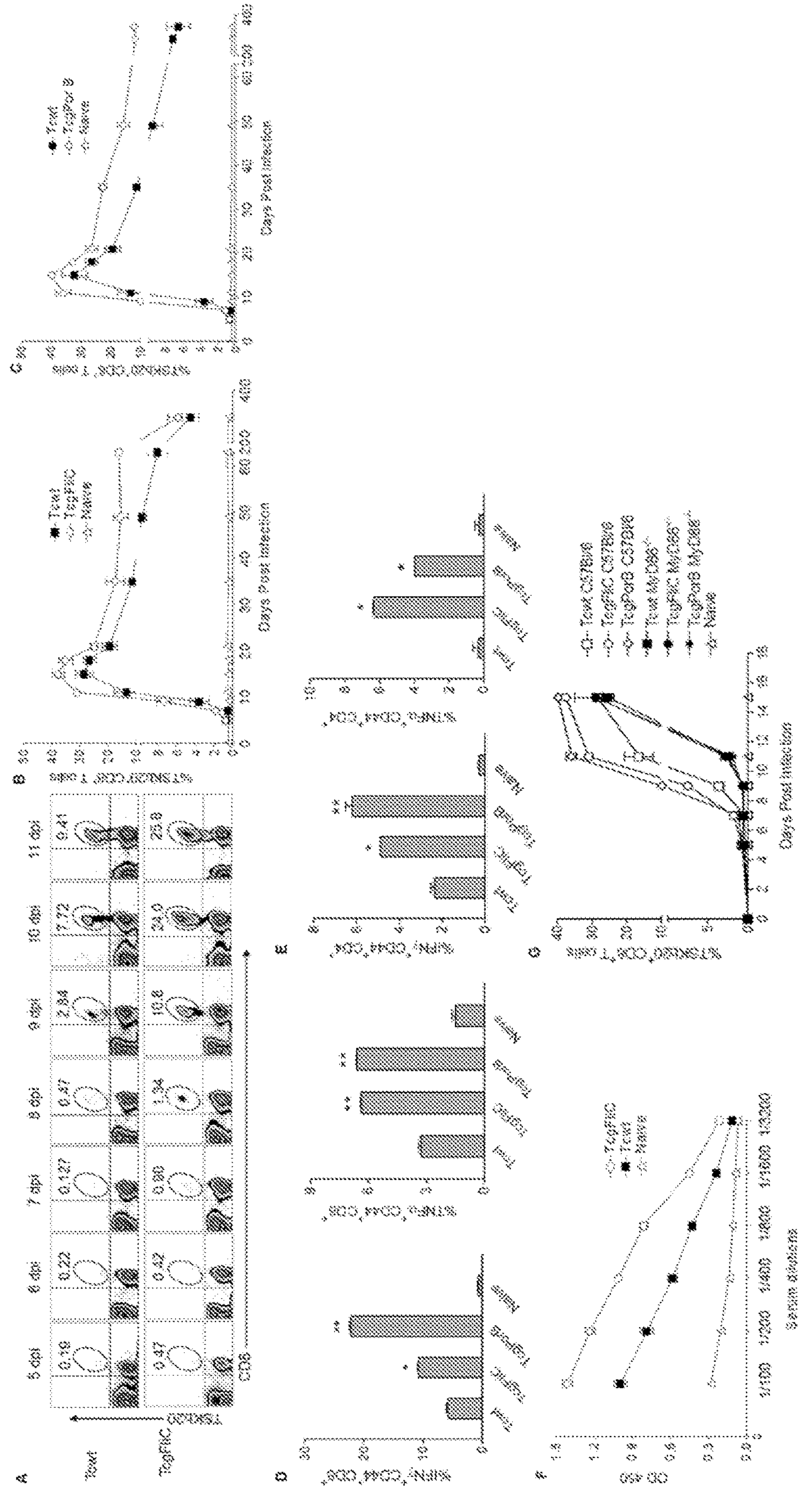
FIG. 6. PAMP transgenesis in *T. cruzi* enhances the adaptive immune responses in mice. (A) Flow plots showing representative data from early time points post-infection in C57BL/6 mice with Tcwt or TcgFliC, with the numbers inset indicating percentage of TSKb20$^+$ CD8$^+$ T cells. (B) The kinetics of TSKb20$^+$CD8$^+$ T cell frequencies in circulation in TcgFliC compared to Tcwt infection of C57BL/6 mice. Data represented as mean±SEM from one of six separate experiments, with at least six mice/group. (C) The kinetics of TSKb20$^+$ CD8$^+$ T cell frequencies in circulation in TcgPorB compared to Tcwt infection of C57BL/6 mice. Data represented as mean±SEM from one of six separate experiments, with at least six mice/group. (D) The percentage of CD8$^+$ (CD44$^+$) T cells producing IFNγ (left) or TNFα (right) in response to TSKb20 peptide re-stimulation in Tcwt, TcgFliC, or TcgPorB infection of C57BL/6 mice, 180 days post-inoculation. Data represented as mean±SEM from one of three separate experiments, with at least three mice/group. (E) The percentage of CD4$^+$(CD44$^+$) T cells producing IFNγ (left) or TNFα (right) in response to *T. cruzi* whole cell lysate re-stimulation in Tcwt, TcgFliC, or TcgPorB infection in C57B1/6 mice, 180 days post-inoculation. Data represented as mean±SEM from one of three separate experiments, with at least three mice/group. (F) Anti-*T. cruzi* antibody titers in sera of mice infected with Tcwt or TcgFliC in C57B1/6 mice, 30 days post-inoculation. *T. cruzi* trypomastigote whole cell lysate served as the antigen in the ELISA. Data shown as mean±SEM and is representative of two separate experiments, with three mice/group. (G) The kinetics of TSKb20$^+$CD8$^+$ T cell frequency in circulation on Tcwt, TcgFliC, or TcgPorB infection of MyD88$^{-/-}$ or C57B1/6 mice. Data represented as mean±SEM from one of three separate experiments, with 3-10 mice/group. * indicates $p \leq 0.05$, ** indicates $p \leq 0.01$, in each case as determined by student t-test comparing the indicated groups to Tcwt.

The control of *T. cruzi* infection in mice can involve a robust *T. cruzi*-specific $CD8^+$ T cell response. The $CD8^+$ T cell response to *T. cruzi* in C57BL/6 mice is dominated by cells specific for peptides encoded by the trans-sialidase gene family (Martin et al., 2006. *PLoS Pathog* 2:e77). Hence, we can use $TSKb20^+CD8^+$ T cells as a surrogate for the total $CD8^+$ T cell response mounted against *T. cruzi*, and track this response using the $TSKb20/K^b$ tetramers (Martin et al., 2006. *PLoS Pathog* 2:e77). Mice infected with PAMP-transgenic *T. cruzi* mounted a more rapid (FIG. 6A) and significantly stronger $TSKb20^+$ $CD8^+$ T cell response that was also maintained at higher levels throughout the infection (FIGS. 6B and 6C) relative to wild-type infected mice. This potentiation of T cell responses by PAMP-transgenic *T. cruzi* was also evident in the IFNγ and TNFα production by antigen-experienced $CD8^+$ (FIG. 6D) and $CD4^+$ (FIG. 6E) T cells. Infection with PAMP-transgenic *T. cruzi* also elicited higher serum levels of *T. cruzi* specific antibodies compared to infection with Tcwt parasites (FIG. 6F).

To reaffirm that the enhanced adaptive immune responses observed with PAMP transgenesis in *T. cruzi* were indeed dependent on signaling through pattern recognition receptors (PRRs) targeted by the transgenic PAMPs, we infected $MyD88^{-/-}$ mice, which are deficient in the primary adaptor for multiple TLRs and are unresponsive to TLR 5, TLR 1/2, or (IL-1β from) NAIP5/ipaf stimulation. The *T. cruzi*-infected $MyD88^{-/-}$ mice showed a delayed generation of TSKb20-specific T cells relative to wild-type mice with the pattern of responses being similar regardless of expression of the bacterial PAMPs (FIG. 6G). This result indicates that the enhanced adaptive immune response to *T. cruzi* conferred by PAMP transgenesis is a result of increased triggering of host PRRs and the consequential effects downstream of MyD88 signaling.

Continuous Expression of FliC is Required to Sustain the Enhanced Adaptive Immunity A canonical concept in immunology is that strong innate immunity invokes more potent adaptive immune responses. This concept is supported by many studies demonstrating that co-delivery of TLR-ligands with antigens or vaccines significantly boosts adaptive immune responses. However, to our knowledge, no studies have directly investigated the impact on adaptive immunity of a transient expression of PAMPS at the initiation of infection compared to a continuous presence of PAMPs throughout the course of infection. Given that PAMP-transgenesis in *T. cruzi* not only initiated a more rapid TSKb20$^+$CD8$^+$ T cell response in mice but also resulted in a response that was maintained at unusually high levels, PAMPs may have a continuous instructive role in maintaining strong adaptive immune responses.

Figure 7:
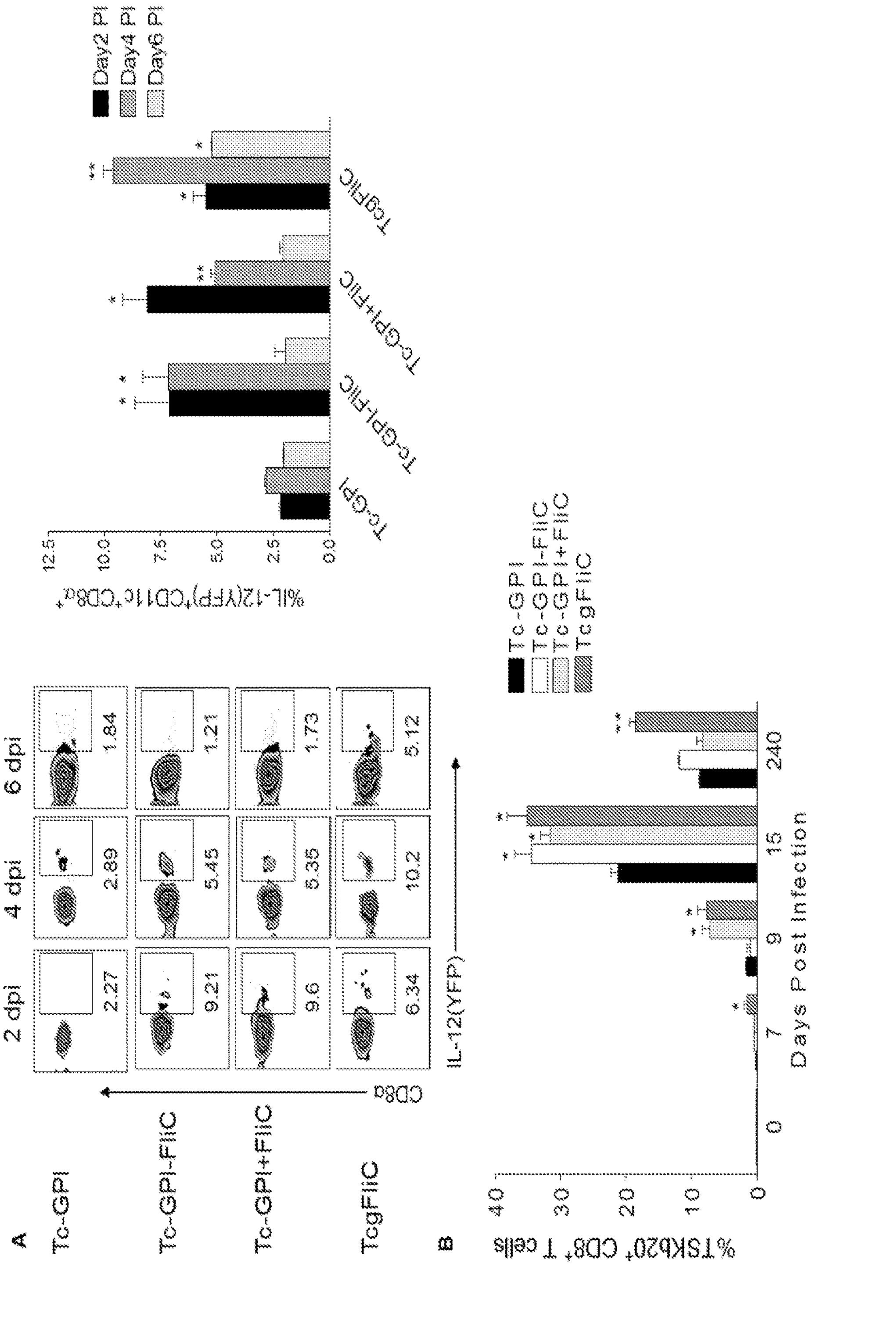
FIG. 7. Continuous expression of FliC is required to sustain the enhanced adaptive immunity. (A) The proportions IL-12 producing cDCs recruited into the draining lymph nodes on various days after infection with *T. cruzi* having FliC temporarily surface-anchored (Tc-GPI-FliC), co-inoculated with (Tc-GPI+FliC), or constitutively expressed in (TcgFliC), compared to the background strain (Tc-GPI) in IL-12yet40 reporter mice. The flow panel shows representative flow plots, with the numbers inset indicating the % IL-12$^+$ cDCs. Data are represented as mean±SEM from one of three separate experiments, with at least three mice/group/time point. (B) TSKb20$^+$CD8$^+$ T cell frequency in circulation on Tc-GPI, Tc-GPI-FliC, Tc-GPI+FliC or TcgFliC infection of C57BL/6 mice. Data represented as mean±SEM from one of three separate experiments, with three mice/group. * indicates $p \leq 0.05$, ** indicates $p \leq 0.01$, in each case as determined by student t-test comparing the indicated groups to Tc-GPI at the corresponding time points.
Figure 8:
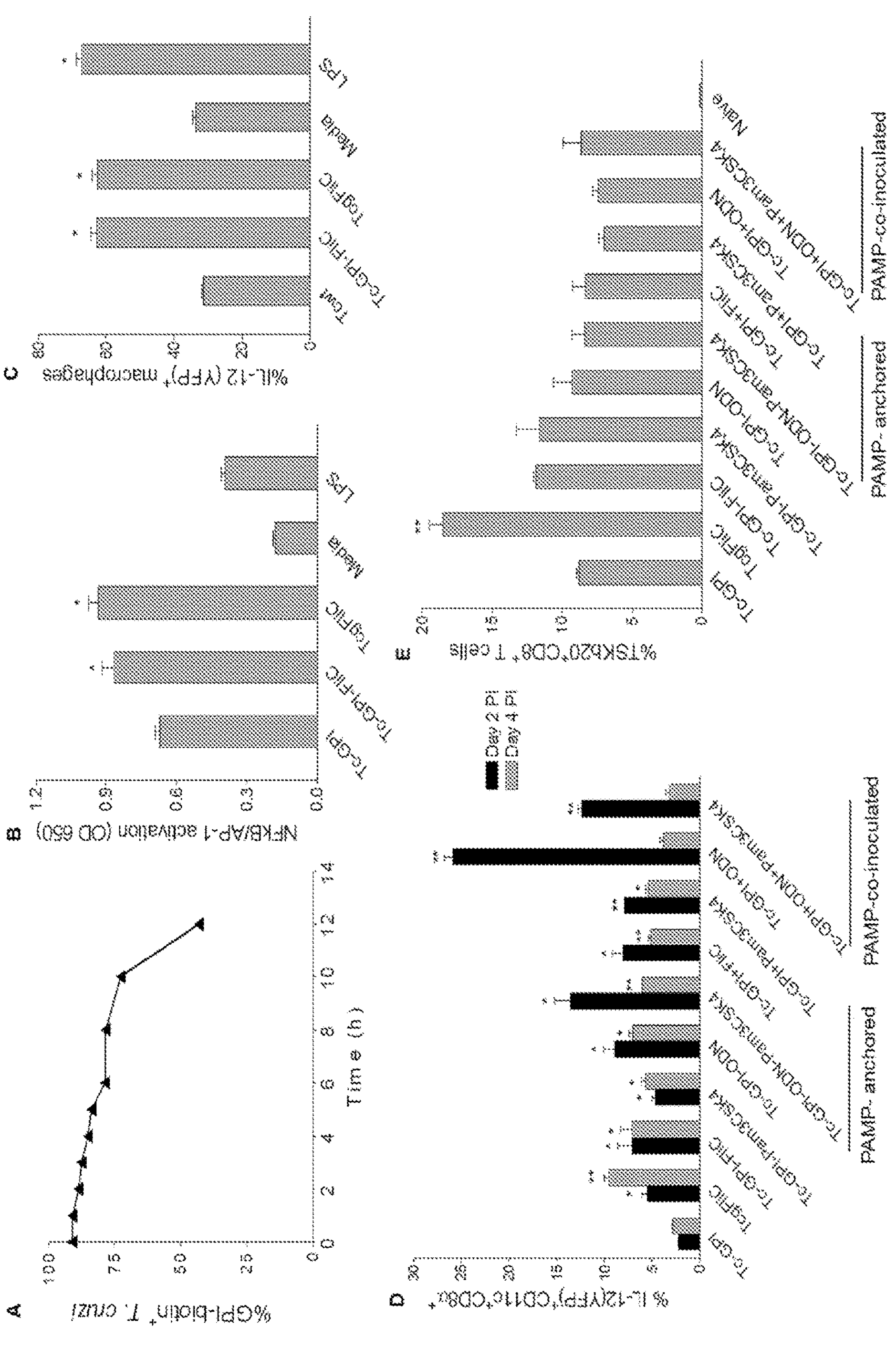
FIG. 8. Continuous expression of FliC sustains the enhanced adaptive immunity. (A) Percentage of *T. cruzi* retaining the GPI-biotin at various time points post surface-anchoring, when maintained at 37° C. as determined by flow cytometry. Data are representative of two separate trials. (B) NFkB/AP-1 activation in reporter cells incubated with Tc-GPI, Tc-GPI-FliC, or TcgFliC trypomastigotes for 12 hours. Media or *E. coli*-derived LPS served as negative and positive controls, respectively. Data represented as mean±SEM from one trial. * indicates $p < 0.05$ as determined by student t-test comparing the indicated groups to Tc-GPI. (C) The proportion of peritoneal exudate macrophages with induced IL-12 production on incubation with Tcwt, Tc-GPI-FliC, or TcgFliC trypomastigotes for 18 hours. Media or *E. coli*-derived LPS served as negative and positive controls, respectively. Data represented as mean±SEM from two separate trials. * indicates $p \leq 0.05$ as determined by student t-test comparing the indicated groups to Tcwt. (D) The percentage of IL-12 producing cDCs recruited into the draining lymph nodes observed on various days after infection with *T. cruzi* having the indicated PAMPs temporarily anchored on, co-inoculated with, or constitutively expressed (TcgFliC), compared to the background strain (Tc-GPI), in IL-12yet40 reporter mice. Data are represented as mean±SEM from one of two separate experiments, with at least three mice/group/time point. (E) The TSKb20$^+$CD8$^+$ T cell frequency in circulation on infection with *T. cruzi* having the indicated PAMPs temporarily anchored on, co-inoculated with, or heterologously over-expressed (TcgFliC), compared to the background strain (Tc-GPI) in C57BL/6 mice, 240 days post infection. Data represented as mean±SEM from one of three separate experiments, with three mice/group. In (D) and (E), * indicates $p \leq 0.05$, ** indicates $p \leq 0.01$, in each case as determined by student t-test comparing the indicated groups to Tc-GPI, at the corresponding time points.

To determine the consequences of transient versus continuous expression of PAMPs on adaptive immune responses to *T. cruzi*, we tethered various PAMPs to *T. cruzi* using GPI-anchors. Initial experiments showed that molecules linked in this fashion were readily incorporated into the surface of trypomastigotes of *T. cruzi* and had a half-life of approximately 12 hours (FIG. 8A). The signaling potency of FliC delivered by the GPI tether (Tc-GPI-FliC) or by endogenous expression (TcgFliC) was equivalent, as indicated by their similar abilities to induce NFkb/AP-1 activation in reporter cells (FIG. 10B) or IL-12 production in peritoneal exudate macrophages (FIG. 8C). Additionally, Tc-GPI-FliC, TcgFliC, or native FliC co-inoculated with *T. cruzi* all potentiated similar innate immune responses to *T. cruzi* in vivo (FIG. 7A), and resulted in nearly identical peak TSKb20$^+$CD8$^+$ T cells responses (FIG. 7B). Only in the infection with TcgFliC, however, was the TSKb20-specific response maintained above the level of the Tcwt infection into the chronic stage (FIG. 5B). The delivery of other individual or combinations of PAMPs with *T. cruzi* infection by GPI-anchors or by co-inoculation enhanced innate (FIG. 8D) immune responses in mice—some much more strongly than TcgFliC. But only infection with the PAMP-transgenic *T. cruzi* resulted in the long-term maintenance of the enhanced adaptive responses (FIG. 8E). Thus, continued expression of PAMPs acts to maintain stronger adaptive immune responses, exceeding those elicited by transient PRR engagement at the initiation of infection.

FliC Transgenesis Enhances Control of *T. cruzi* Infection in Mice

To investigate the impact of the PAMP-induced enhancement of innate and adaptive immune responses on the parasite control during the course of *T. cruzi* infection, we first monitored the phenotype of *T. cruzi*-specific CD8$^+$ T cells in these mice. Drug-induced cure of *T. cruzi* infection results in a gradual shift in the TSKb20$^+$CD8$^+$ T cells from a predominant T-effector phenotype)(CD127$^{lo}$) to a majority T-central memory ($T_{CM}$)-like (CD127$^{hi}$) phenotype, accompanied by a decrease in the frequency of CD8$^+$ T cells expressing KLRG1, a marker for repeated antigenic stimulation.

Figure 9:
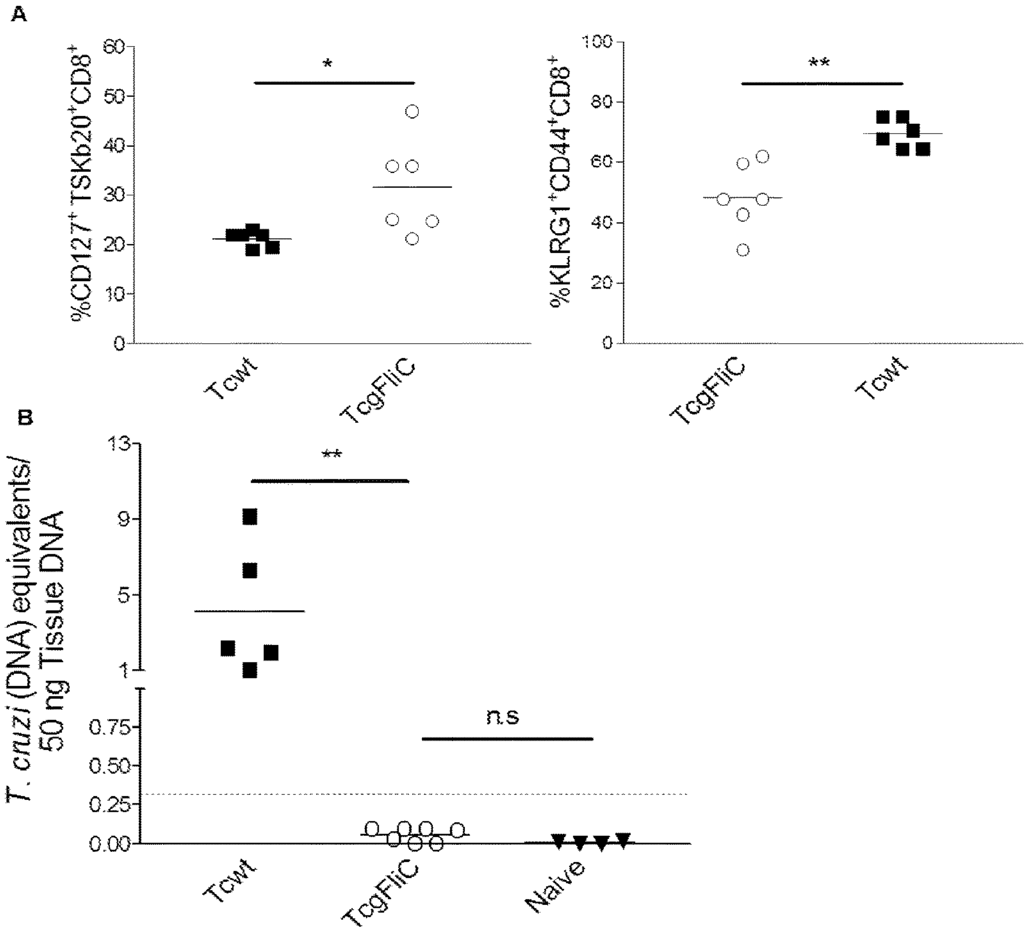
FIG. 9. FliC transgenesis enhances control of *T. cruzi* infection in mice as indicated by an increase in central memory phenotype T cells and reduced parasite load. (A) Frequency of CD8$^+$ T cells in circulation having Tcm like phenotype (CD127$^{hi}$ TSKb20$^+$ CD8$^+$ (left) and KLRG1$^{lo}$ CD44$^+$ CD8$^+$ (right)), in Tcwt or TcgFliC infected C57BL/6 mice, 296 days post-inoculation. Data represents three separate experiments with 3-6 mice/group. (B) *T. cruzi* DNA in skeletal muscle of C57BL/6 mice inoculated with Tcwt or TcgFliC as determined by quantitative real-time PCR, 400 days post-inoculation. Horizontal bars represent the mean. Naïve mice served as control. The dotted line represents the threshold of detection for the assay. Data are representative of five separate experiments with at least six mice/group. * indicates $p \leq 0.05$, ** indicates $p \leq 0.01$, and n.s indicates $p > 0.05$, in each case as determined by student t-test.

At 296 days post-inoculation, TcgFliC-infected mice exhibited higher proportions of $T_{cm}$ among the TSKb20$^+$ CD8$^+$ T cells and decreased numbers of KLRG1$^+$(CD44$^+$) CD8$^+$ T cells in comparison to mice infected with wild-type *T. cruzi* (FIG. 9A), suggesting more effective control of the infection with TcgFliC. This conclusion was confirmed using qPCR to measure *T. cruzi* DNA in muscle tissue from these mice. At 400 days post-inoculation, *T. cruzi* DNA was undetectable in mice infected with TcgFliC, but was consistently detected in tissues from Tcwt infected mice (FIG. 9B).

Figure 10:
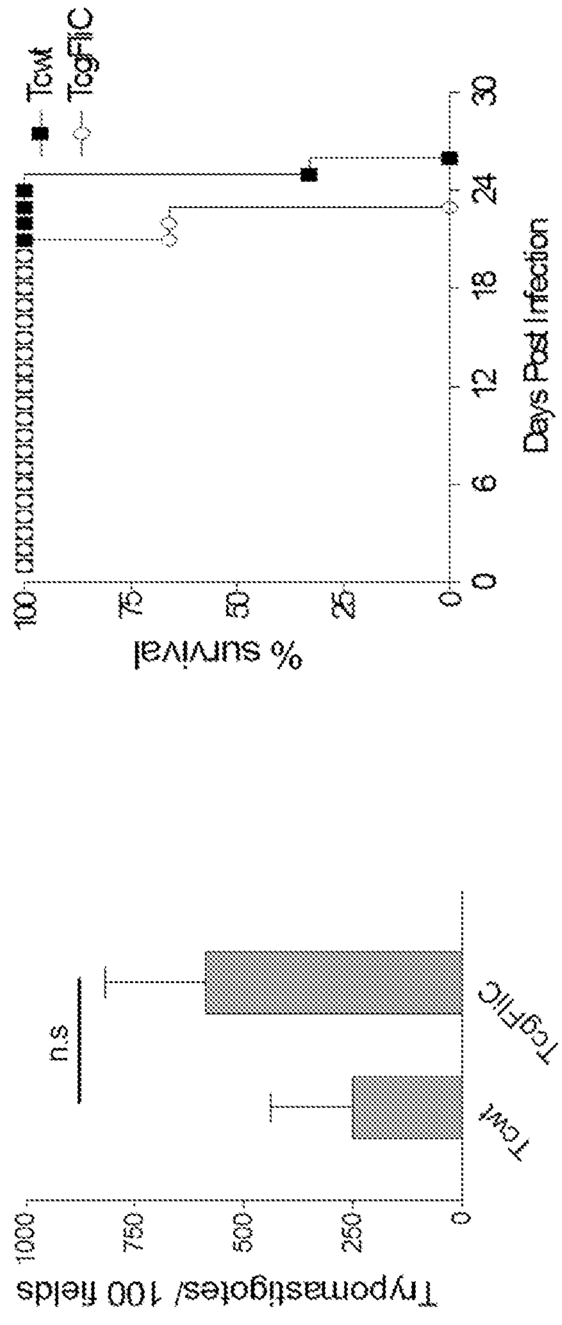
FIG. 10. (A) PAMP transgenesis does not influence the virulence of *T. cruzi*. (A) *T. cruzi* trypomastigotes in circulation observed in Tcwt-infected or TcgFliC-infected IFNγ$^{-/-}$ mice, 21 days post-inoculation. Data are represented as mean±SEM from one of two separate experiments, with at least three mice/group. (B) Mortality observed in Tcwt or TcgFliC infected IFNγ$^{-/-}$ mice. Data representative of at least two separate experiments with three mice/group. n.s indicates $p > 0.05$, as determined by student t-test.

Immunosuppression can reveal otherwise undetectable infection and be a definitive measure of drug-induced cure in *T. cruzi* infection. One of three TcgFliC-infected mice immunosuppressed with cyclophosphamide exhibited no detectable parasites after immunosuppression, indicating clearance of the infection (data not shown). The enhanced control of the TcgFliC infection relative to wild-type *T. cruzi* infection was not due to a decrease in virulence of the FliC-transgenic parasites, as IFN$\gamma^{-/-}$ mice infected with TcgFliC or Tcwt showed similar peripheral blood parasite loads and mortality patterns (FIG. 10). Taken together, these data indicate that FliC transgenesis potentiates adaptive immune responses and facilitates control and clearance of *T. cruzi* infection.

One paradigm in immunology is that innate immune mechanisms detect microbial infections through their characteristic PAMPs and trigger the specific antimicrobial host defense responses appropriate to that infection. Once initiated, these pathogen-specific adaptive immune responses bring about control of the infection and, often, a long-term specific immunological memory. However, we have very limited knowledge of the role of PAMPs in influencing the adaptive immunity beyond its initiation, in large part because, by their very nature, PAMPS are crucial for pathogen survival and thus cannot be turned off during an infection. In this study we provide unequivocal evidence that the expression of classical bacterial PAMPS in the protozoan pathogen *T. cruzi* results in substantially enhanced innate and adaptive immune responses and more efficient pathogen control. These data add to the wealth of information indicating that *T. cruzi* has an extremely quiet entry into hosts and a considerably delayed induction of anti-parasitic immune responses.

Though PAMPs are highly conserved structures that are extremely difficult for pathogens to alter or sacrifice, there is some plasticity in PAMP display. For example, host detection of LPS in *Porphyromonas gingivalis* and *Escherichia coli* is modulated by differential acylation of lipid-A, while *Yersinia pestis* synthesizes LPS-lipid A that is a poor TLR 4 ligand. *Helicobacter pylori* produces a flagellin that is non-stimulatory to TLR 5 and *Pseudomonas aeruginosa* down-regulates its flagellin expression in airway passages. Although it is unlikely that any pathogen will be able to make all its PAMPs entirely invisible to the immune system, potential PAMPs could be rendered immunologically inconsequential by concealing or modifying the PAMP without significantly impacting pathogen biology.

Multiple PAMPs (e.g., GPI anchors, *T. cruzi* DNA, GIPL-ceramide) have been attributed to *T. cruzi* but these molecules seem to be relatively insignificant to the downstream immune responses generated. The apparent insignificance of *T. cruzi* PAMPs may be due, at least in part, to these putative PAMPs being "hidden" from their respective TLRs in live, intact *T. cruzi*. However, when strong bacterial PAMPs are transgenically expressed and released by *T. cruzi*, significantly improved innate and adaptive immune responses are generated. Thus, the failure of *T. cruzi* to display potent PAMPs may indeed be another example of innate immune evasion employed by pathogens.

The observed evasion of innate immune responses may not only be important in delaying the adaptive immune response (thus allowing for firm establishment of the infection), but also may promote the persistence of *T. cruzi*. In the presence of a bacterial PAMP, *T. cruzi* infection is better controlled and even completely cleared in some cases. Complete clearance of *T. cruzi* infection is normally extremely rare. Given the increased level of *T. cruzi*-specific $CD8^+$ T cells with a Tcm phenotype and the nearly undetectable tissue parasite load in mice infected with PAMP transgenic *T. cruzi*, most of these mice would eventually cure these infections if allowed sufficient time. Importantly, this enhanced control of *T. cruzi* infection derived from expression of bacterial PAMPs is not associated with any evidence of increased immunopathology.

The relative absence of PAMPs in *T. cruzi* provided a unique opportunity to study the importance of PAMP expression beyond the early induction of adaptive immune responses. Though there is a wealth of literature demonstrating how the strength of innate immunity determines the potency of adaptive immune responses, few studies have focused on the impact of innate immune responses on adaptive immunity once an infection is established. When potent bacterial PAMPs were either co-inoculated with, temporarily surface-anchored on, or constitutively expressed by the invading *T. cruzi*, the resulting adaptive immune responses were not only accelerated, but also peaked at levels that were significantly above the levels seen in mice infected with wild-type *T. cruzi*. It was only when *T. cruzi* perpetually expressed the PAMPs, however, that the stronger adaptive immune responses were maintained throughout the course of the infection, eventually leading to a better control of the pathogen and sterile clearance in some cases.

Without wishing to be bound by any particular theory, the quality, quantity, and longevity of T and B cells may be potentiated by the generally enhanced inflammatory milieu and/or the improved antigen processing and presentation by more highly activated APCs resulting from continuing PAMP exposure. Transgenic expression of FliC and PorB induced similar boosting of immune responses. Moreover, transgenic expression of TcgFliC further corresponded with better parasite control. FliC is distinctive in its ability to induce IL-1β through the intracellular NAIP5/ipaf receptor stimulation. Given that *T. cruzi* spends the majority of its time in vertebrates in the cytoplasm of host cells that are likely to express the NAIP5/ipaf receptor, it is possible that NAIP5/ipaf-IL-1β activation contributes to enhanced recognition and control of TcgFliC-infected cells. IL-1β levels have also been shown to correlate with $CD8^+$ T cell abundance in adipose tissue, which is a major depot for chronic *T. cruzi* persistence.

A possible confounder in the interpretation of our results is that FliC expressed by TcgFliC may act as a target antigen for adaptive immune responses, contributing to the control of FliC-expressing parasites. However, the absence of detectable FliC-specific $CD4^+$ or $CD8^+$ T cells in TcgFliC-infected mice argues against this possibility. Additionally, *T. cruzi* expressing the highly immunogenic chicken ovalbumin (OVA) protein that induces very strong OVA-specific T cells does not appear to be controlled any better than wild-type *T. cruzi*, further suggesting against control of *T. cruzi* infection through an adaptive response to a target antigen.

The deficiency of effective PAMPs in *T. cruzi* may be only one of the several factors that contribute to the marked delay in initiation of anti-*T. cruzi* immune responses. An additional trigger for induction of adaptive responses is exposure of damage associated molecular patterns (DAMPs). Revelation of DAMPs from either host or *T. cruzi* would not be expected until 4-5 days post-infection, with the initial round of exit of *T. cruzi* from infected host cells.

Thus, innate immune responses may have an extended instructive role on adaptive immunity, thus playing an even more significant part in the effective control of pathogens than was previously appreciated. The inability of classical adjuvants to productively stimulate innate immunity and to generate long-lasting T cell responses has been a hurdle in the development of T-cell-based vaccines. Our observation that PAMP transgenesis generates stronger and longer lasting specific immunity may aid in the development of better vaccination strategies, especially of live attenuated vaccines.

Figure 11:
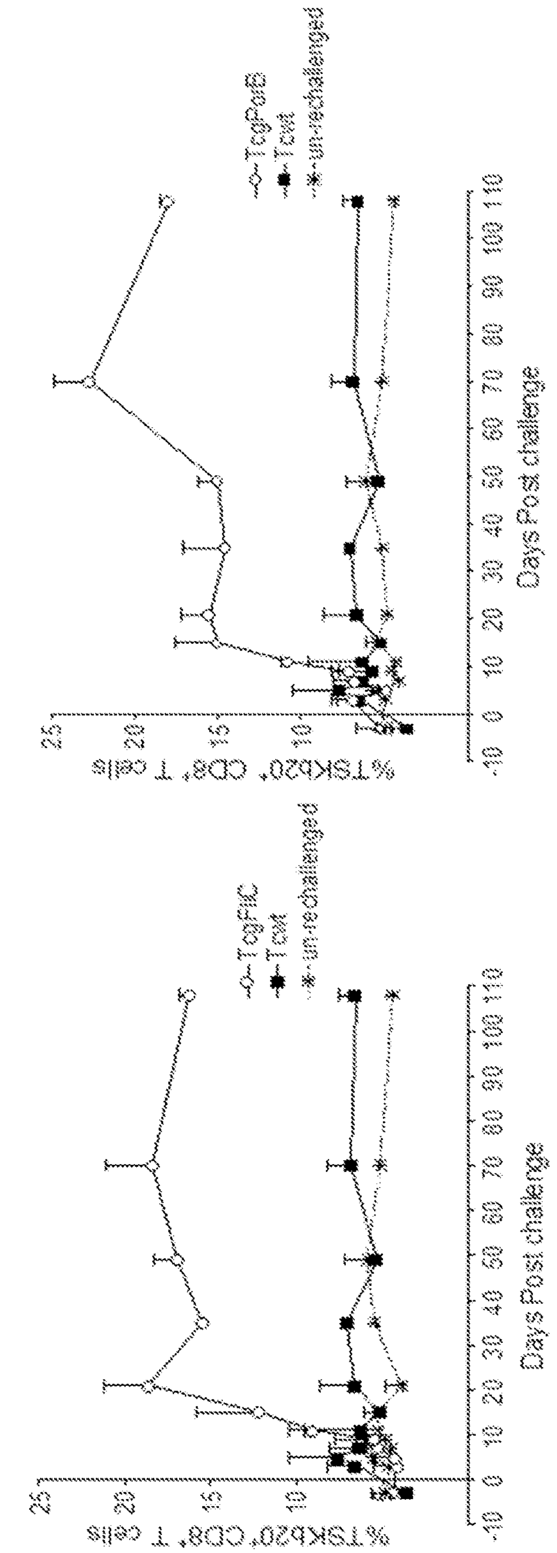
FIG. 11. Inoculation of previously infected mice with TcgFliC parasites markedly boosts the *T. cruzi*-specific T cell response. Mice chronically infected with wild-type *T. cruzi* (>300 days post-inoculation) were rechallenged with $10^4$ TcgFliC, TcgPorB, or Tcwt trypomastigotes in the foot-pad. The level of *T. cruzi*-specific (TSKb20$^+$) CD8$^+$ T cells was then measured. The mice challenged with Tcwt had a brief and modest enhancement in *T. cruzi*-specific T cell responses but mice receiving either TcgFliC or TcgPorB experienced a threefold to fivefold increase in response that persisted for at least 100 days. Data represents one of three separate experiments.
Figure 12:
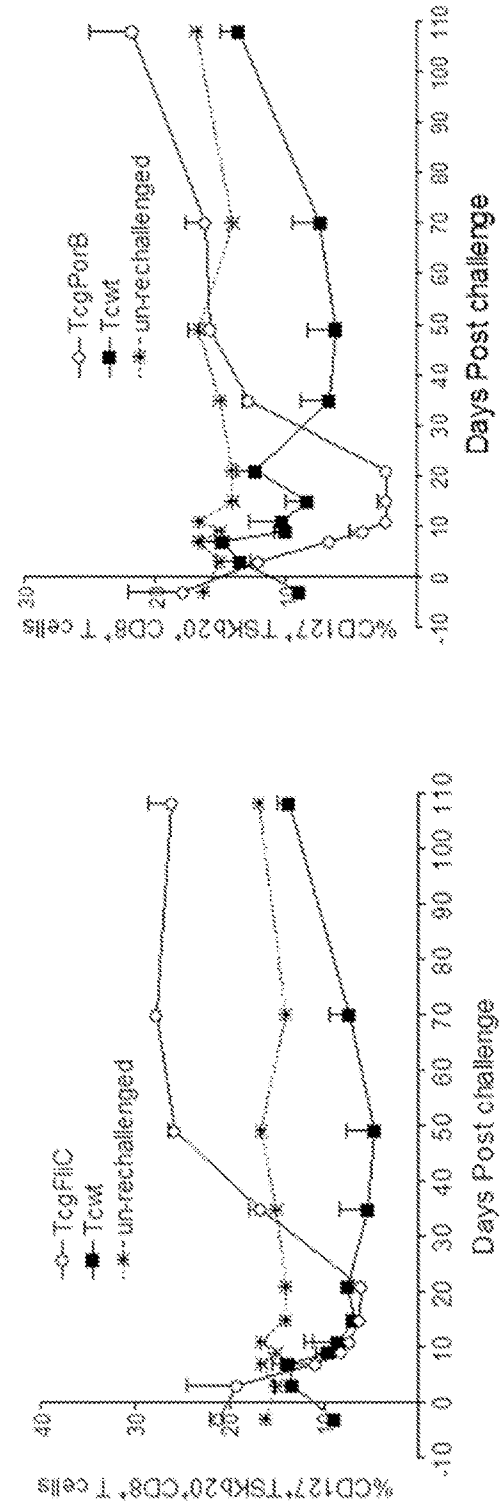
FIG. 12. Mice "vaccinated" with TcgFliC parasites show an increase in CD127 expression on their *T. cruzi*-specific CD8+ T cells, indicative of the relative absence of antigen stimulation and thus an enhanced clearance of parasites in the mice boosted with PAMP-transgenic *T. cruzi*. Mice chronically infected with wild-type *T. cruzi* (>300 days post-inoculation) were rechallenged with $10^4$ TcgFliC, TcgPorB, or Tcwt trypomastigotes in the foot-pad and the TSKb20$^+$ CD8$^+$ T cell population was analyzed for the expression the central memory T cell marker CD127. The increase in CD127 expression is indicative of the relative absence of antigen stimulation and thus an enhanced clearance of parasites in the mice boosted with PAMP-transgenic *T. cruzi*. Data represents one of three separate experiments.
Figure 13:
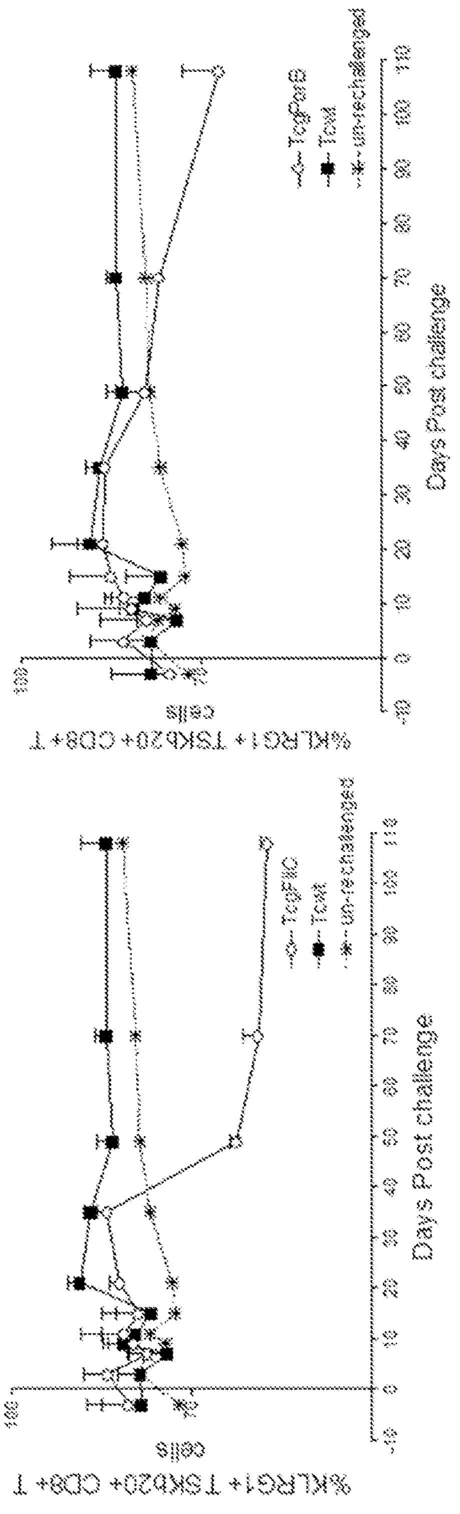
FIG. 13. Mice "vaccinated" with TcgFliC parasites show a decrease KLRG1 expression on their *T. cruzi*-specific CD8+ T cells, indicative of a decrease in antigen stimulation and thus an enhanced clearance of parasites in the mice boosted with PAMP-transgenic *T. cruzi*. Mice chronically infected with wild-type *T. cruzi* (>300 days post-inoculation) were rechallenged with $10^4$ TcgFliC, TcgPorB, or Tcwt trypomastigotes in the foot-pad and the TSKb20$^+$ CD8$^+$ T cell population was analyzed for the expression the effector T cell marker KLRG1. The decrease in KLRG1 expression is indicative of the relative absence of antigen stimulation and thus an enhanced clearance of parasites in the mice boosted with PAMP-transgenic *T. cruzi*. Data represents one of three separate experiments.
Figure 14:
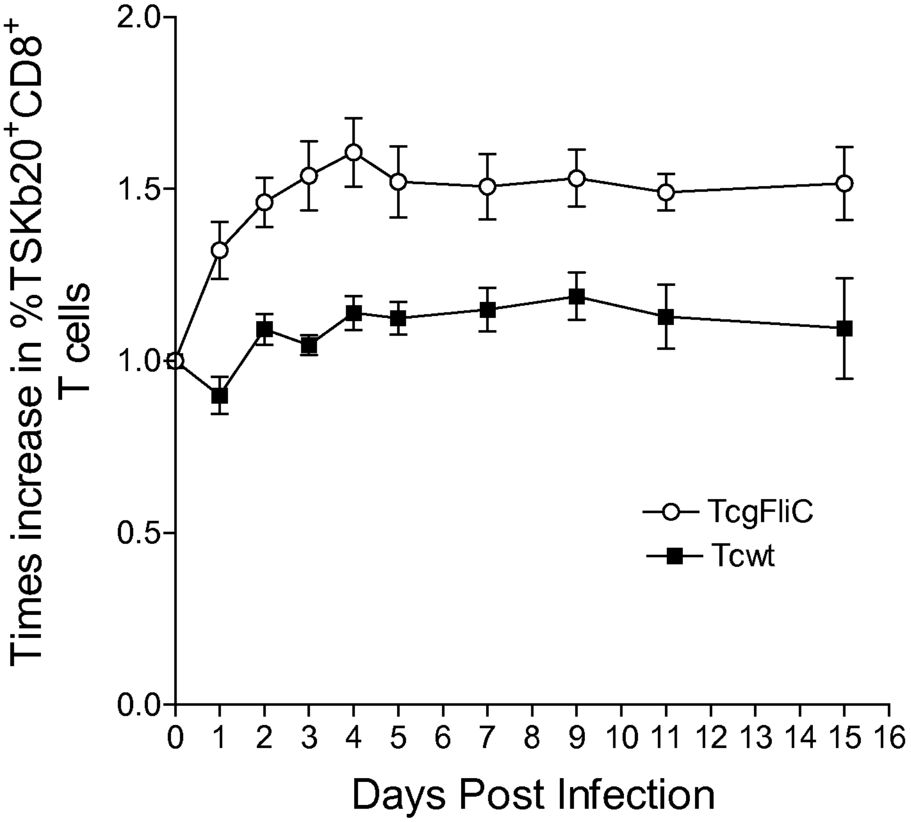
FIG. 14. Change in *T. cruzi*-specific T cell response expressed as fold-increase following Tcwt or TcgFliC (flagellin-expressing *T. cruzi*) challenge. Data represents one of four separate experiments.

For example, rechallenge of chronically infected mice with PAMP-expressing (either flagellin-expressing (TcgFliC) or porin-expressing (TcgPorB)) transgenic *T cruzi* elicited a stronger, more sustained recall immune response. (FIG. 11 and FIG. 14). Moreover, FIG. 12 shows an increase in the proportion of $CD127^+TSKb20^+$ $CD8^+$ T cells in mice rechallenged with PAMP-transgenic *T. cruzi* compared to un-rechallenged mice or mice rechallenged with wild-type *T. cruzi*. As described earlier, the higher proportion of $CD127^+TSKb20^+$ $CD8^+$ T cells indicate better control or clearance of *T. cruzi* infection. FIG. 13 shows a decrease in the proportion of $KLRG1^+TSKb20^+$ $CD8^+$ T cells in mice rechallenged with PAMP-transgenic *T. cruzi* compared to un-rechallenged mice or mice rechallenged with wild-type *T. cruzi*. The decrease in the proportion of $KLRG1^+$ $TSKb20^+$ $CD8^+$ T cells also may be considered an indicator of progressive clearance of *T. cruzi* infection.

Figure 15:
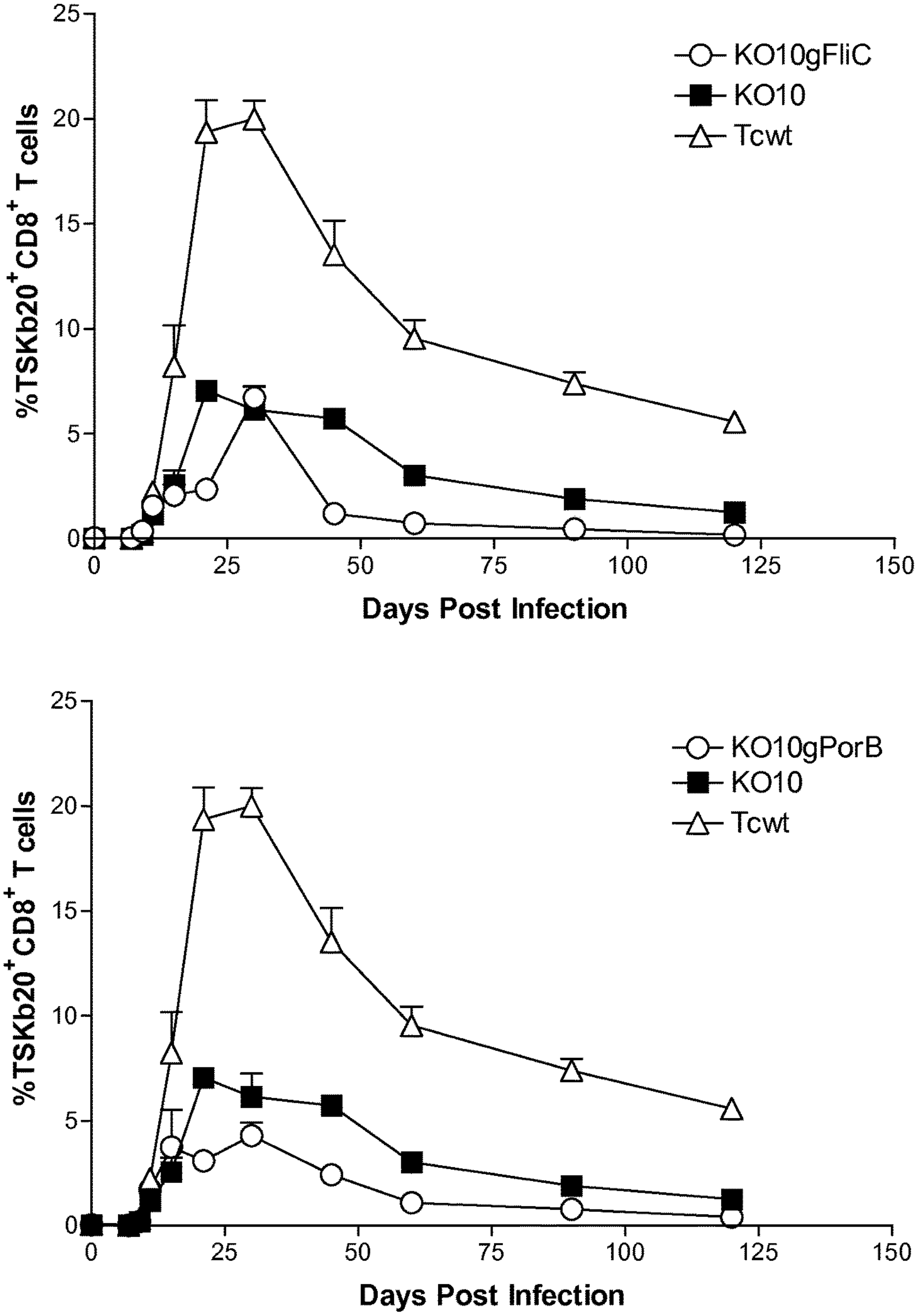
FIG. 15. In contrast to wild-type parasites expressing FliC (TcgFliC) that may persist for a long-term in mice, *T. cruzi* deficient in a gene encoding a protein of unknown function (KO-10) have much reduced virulence and limited persistence in mice. As a consequence, KO-10 parasites also induce a much reduced *T. cruzi*-specific T cell response, which is not enhanced by the expression of either FliC or PorB. Data represents one of two separate experiments.
Figure 16:
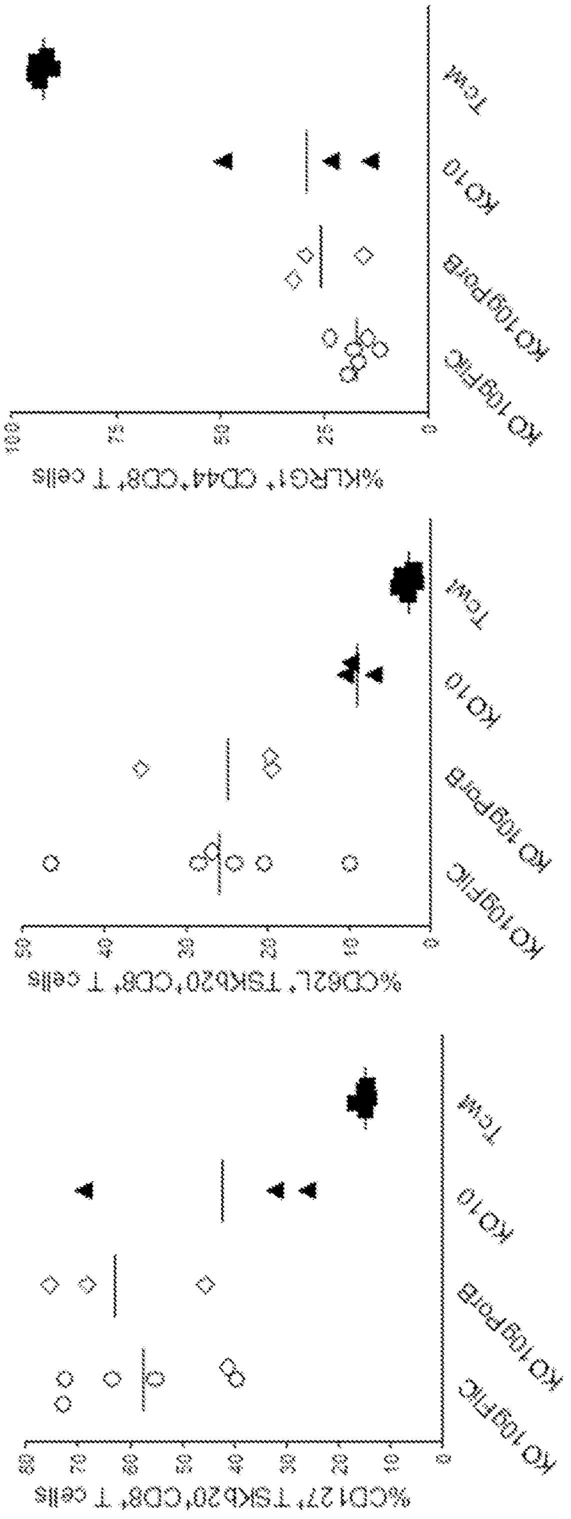
FIG. 16. PAMP transgenic KO10 parasites also appear to be more readily controlled than either wild-type or KO-10 parasites, as suggested by increased central memory markers (CD127 and CD62L) and reduced activation markers (KLRG1) on *T. cruzi*-specific (TSKb20$^+$ CD8$^+$) T cells FIG. 17. KO-10/KO-10gFliC parasites delivered as a therapeutic vaccine induce enhanced control of an ongoing infection (520 days post infection, at time of vaccination) as indicated by the much reduced to negligible parasite tissue load detected 230 days post vaccination. Horizontal bars represent the mean. Not vaccinated (Unrechallenged) mice served as controls. The dotted line represents the threshold of detection for the assay. Data are representative of three separate experiments with at least 3-6 mice/group. The indicated p values were determined by student t-test.
Figure 17:
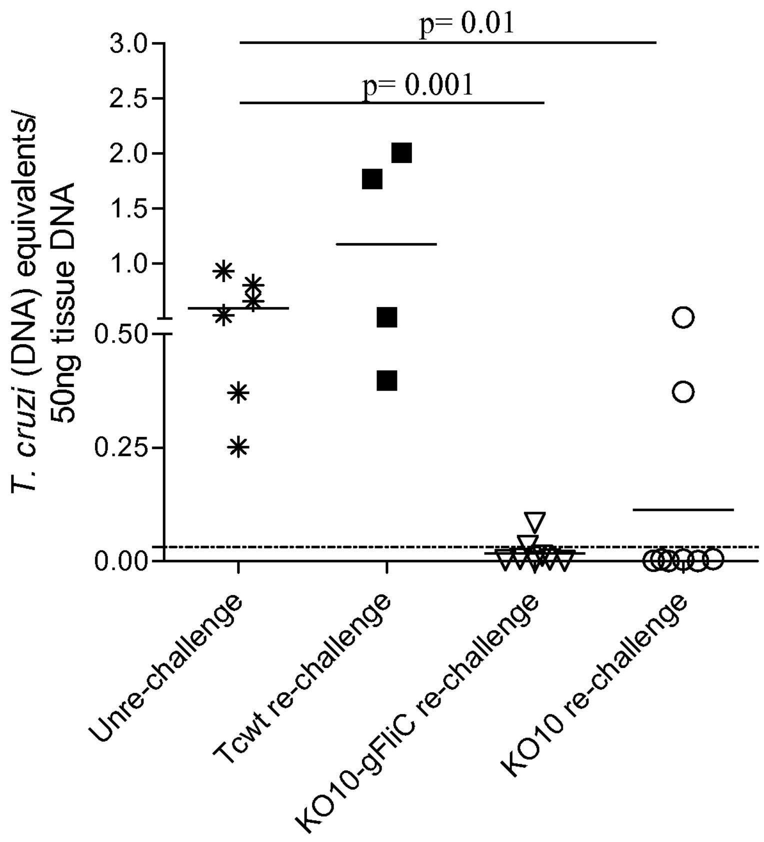

*T. cruzi* deficient in a gene encoding a protein of unknown function (KO10) have much reduced virulence and limited persistence in mice. As a consequence, KO10 parasites also induce a much reduced *T. cruzi*-specific T cell response which is not enhanced by the expression of either FliC (KO10gFliC) or PorB (KO10gPorB) (FIG. 15). However, PAMP transgenic KO10 parasites appear to be more readily controlled than either Tcwt or KO10 parasites, as suggested by increased central memory markers (CD127 and CD62L) and reduced activation markers (KLRG1) on *T. cruzi*-specific ($TSKb20^+$ $CD8^+$) T cells (FIG. 16). As a consequence of the recall immune response generated, rechallenging chronically infected mice with KO10, KO10gFliC or KO10gPorB induced a better control of *T. cruzi*. KO10/KO10gFliC parasites delivered as a therapeutic vaccine induced enhanced control of an on-going infection (520 days at time of vaccination) as indicated by the much reduced to negligible parasite tissue load detected 230 days post vaccination (FIG. 17), indicating the potential of therapeutic live-vaccinations in persistent infections.

Thus, in one aspect, this disclosure describes a composition that includes a transgenic pathogen (e.g., an infectious pathogen or other cell such as, for example, a tumor cell) that expresses a heterologous pathogen associated molecular pattern (PAMP) or a heterologous damage associated molecular patterns (DAMP). As used herein, "heterologous" refers to a PAMP that is not natively produced by the pathogen.

The compositions described herein can be employed in connection with any "live vaccine" (e.g., polio or live vaccine vector (vaccinia, cytomegalovirus, adenovirus, etc.)). Most vaccines administered to humans are not given as live vaccines for safety reasons. Some, however, may be made safer and more acceptable with PAMP expression. Moreover, the compositions described herein may be employed in connection with live vaccines administered to animals including, for example, livestock and/or companion animals. In an individual with a persistent infection—i.e., the individual is already infected by a pathogen—therapeutic administration of a composition that includes a live pathogen genetically modified as described herein can amplify the individual's existing immune response to the infecting pathogen.

The PAMP can be any PAMP that can induce an innate immune response to a pathogen that expresses the PAMP, acting through pattern recognition receptors (PRRs) on host cells. Exemplary PAMPs include, but are not limited to, Toll-like receptor (TLR), Nod-like receptor (NLR), C-type lectin receptor (CLR) or RIG-I-like receptor (RLR) ligands. Suitable TLRs include, for example, TLR 1, TLR 2, TLR 3 TLR 4, TLR 5, TLR 6, TLR 7, TLR 8, TLR 9, TLR 10, TLR 11, TLR 12, and TLR 13, Suitable NLRs include, for example, Neuronal Apoptosis Inhibitory Protein 5/IL-1β-converting enzyme protease-activating factor (NAIP5/Ipaf) or NACHT, LRR and PYD domains-containing protein 3 (NALP3). Suitable RLRs include Retinoic acid-inducible gene 1 (RIG-I), Melanoma Differentiation-Associated protein 5 (MDA5) or RIG-I-like receptor 3 (LGP2). Suitable CLRs include Dec205, Dectin-1, Dectin-2, DNGR-1, etc.

The DAMP can be any DAMP that can induce an innate immune response to a cell that expresses the DAMP. Exemplary DAMPs include, but are not limited to DNGR-1, or HMGB1 receptor(s).

In some embodiments, the cell expressing the PAMP or DAMP may be a cancer cell or an infectious pathogen—e.g., *T. cruzi*. In such cases, the pathogen may be attenuated. Such embodiments can have utility as a therapeutic or prophylactic agent that may be administered to a subject having, or at risk of having, an infection of a non-attenuated form of the pathogen. As used herein, a subject having a condition caused by infection by the pathogen refers to a subject exhibiting one or more symptoms or clinical signs of the condition. "Symptom" refers to any subjective evidence of disease or of a patient's condition. "Sign" or "clinical sign" refers to an objective physical finding relating to a particular condition capable of being found by one other than the patient. As used herein, the term "at risk" refers to a subject that may or may not actually possess the described risk. Thus, for example, a subject "at risk" of infectious condition is a subject present in an area where other individuals have been identified as having the infectious condition and/or is likely to be exposed to the infectious agent even if the subject has not yet manifested any detectable indication of infection by the microbe and regardless of whether the animal may harbor a subclinical amount of the microbe.

Accordingly, introduction of the transgenic pathogen can be performed before, during, or after the subject first exhibits a symptom or clinical sign of the condition or, in the case of infectious conditions, before, during, or after the subject first comes in contact with the infectious agent. Treatment initiated after the subject first exhibits a symptom or clinical sign associated with the condition—i.e., therapeutic treatment—may result in decreasing the severity of symptoms and/or clinical signs of the condition, completely resolving the condition, and/or decreasing the likelihood of experiencing clinical evidence of the condition compared to an animal to which the composition is not administered. Similarly, treatment initiated before the subject first exhibits a symptom or clinical sign associated with the condition—i.e., prophylactic treatment—may result in decreasing the severity of symptoms and/or clinical signs of the condition, completely resolving the condition, and/or decreasing the likelihood of experiencing clinical evidence of the condition compared to an animal to which the composition is not administered.

The method includes administering an effective amount of the composition to a subject having, or at risk of having, a particular condition. In this aspect of the invention, an "effective amount" is an amount effective to reduce, limit progression, ameliorate, or resolve, to any extent, the symptoms or clinical signs related to the condition.

A formulation containing the transgenic pathogen may be provided in any suitable form including but not limited to a solution, a suspension, an emulsion, a spray, an aerosol, or any form of mixture. The composition may be delivered in formulation with any pharmaceutically acceptable excipient, carrier, or vehicle. The formulation may further include one or more additives including such as, for example, an adjuvant or an inert carrier (e.g., a nanoparticle), cell culture media, and/or ionic/salt solutions.

The amount of transgenic pathogens administered to a subject can vary depending on various factors including, but not limited to, the weight, physical condition, and/or age of the subject, the route of administration, the immune status of the subject, and/or the specific transgenic pathogen. Thus, the absolute amount of transgenic pathogen included in a given unit dosage form can vary widely, and depends upon factors such as the transgenic pathogen, the therapeutic indication, the species, age, weight and/or physical condition of the subject, as well as the method of administration. Accordingly, it is not practical to set forth generally the amount that constitutes an amount of transgenic pathogen effective for all possible applications. Those of ordinary skill in the art, however, can readily determine the appropriate amount with due consideration of such factors.

In some embodiments, transgenic pathogen may be administered, for example, in a single dose to multiple doses. Because the transgenic pathogen can extend the period of an innate immune response and/or generate long-lasting T cell responses, it may be possible to administer a composition that includes a transgenic pathogen, as described herein, fewer times to control a disease than other conventional therapies. Indeed, the transgenic pathogen can provide an increased innate response compared to the innate response generated by therapy that includes a combination of PAMP (or DAMP) and an attenuated form of the pathogen that is not genetically modified to express the PAMP (or DAMP), regardless of whether the PAMP (or DAMP) is, for example, co-administered with the attenuated form of the pathogen or tethered to the attenuated form of the pathogen.

In another aspect, this disclosure describes a composition that includes a pathogen that is genetically modified to include a polynucleotide that encodes a polypeptide involved in innate immunity. The polypeptide can include a PAMP or a DAMP as described in detail above.

The transgenic pathogen described herein may be formulated in a composition along with a "carrier." As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions.

By "pharmaceutically acceptable" is meant a material that is not biologically or otherwise undesirable, i.e., the material may be administered to an individual along with transgenic pathogen without causing any undesirable biological effects or interacting in a deleterious manner with any of the other components of the pharmaceutical composition in which it is contained.

The transgenic pathogen may be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, intraperitoneal, subcutaneous, etc.), or topical (e.g., intranasal, intrapulmonary, intramammary, intravaginal, intrauterine, intradermal, transcutaneous, rectally, etc.). For example, a composition can be administered to a mucosal surface, such as by administration to, for example, the vaginal, nasal, or respiratory mucosa (e.g., by spray or aerosol). In some embodiments, the composition may be administered orally. In other embodiments, a composition also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing a transgenic pathogen, as described herein, into association with a carrier that constitutes one or more accessory ingredients. In general, a formulation may be prepared by uniformly and/or intimately bringing the transgenic pathogen into association with a liquid carrier, a finely divided solid carrier, or both, and then, if necessary, shaping the product into the desired formulations.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Mice, Parasites, and Infections

C57BL/6, B6.IFNγ-knockout (IFNγ$^{-/-}$), MyD88 Knockout (MyD88$^{-/-}$), B6.IL-12yet40 reporter (IL-12yet40) and IFNγ reporter (Yeti) mice were purchased from The Jackson Laboratory (Bar Harbor, Me.) and maintained in our animal facility under specific pathogen-free conditions. *T. cruzi* epimastigotes were transfected as described previously (Garg et al., 1997. *J Immunol* 158:3293-3302) with pTREX plasmid (Lorenzi et al., 2003. *Gene* 310:91-99) containing the coding sequence of *Salmonella typhimurium* flagellin (FliC), *Neisseria meningitidis* (FAM18 strain) porin (PorB), or *T. cruzi* paraflagellar rod protein 4 (PAR4), with or without fusion to an upstream N-terminal portion of the *T. cruzi* gp72 gene or influenza haemagglutinin (HA)-tag, to generate transgenic *T. cruzi*. All infections were initiated by inoculating Vero-cell-culture-passaged trypomastigote stage *T. cruzi*, intra-peritoneally (i.p) ($10^4$ parasites) or subcutaneously in the ear (s.c) ($5\times10^4$ parasites) or the foot pad (f.p) ($10^4$ parasites). All animal protocols were approved by the University of Georgia Institutional Animal Care and Use Committee.

Reporter Cell Assay for NFkB/AP-1 Activation and IL-12 Production

The ability of various *T. cruzi* strains to induce NFkB/AP-1 activation by TLR stimulation was assayed using THP1-Blue-CD14 reporter cells (InvivoGen, San Diego, Calif.), following the manufacturer's protocol. $10^4$ live *T. cruzi* trypomastigotes were incubated with $2\times10^6$ reporter cells for nine hours at 37° C./5% $CO_2$, and the nuclear translocation of activated NFkB/AP-1 was determined by colorimetrically quantifying the secreted embryonic alkaline phosphatase (SEAP). To determine the IL-12 production induced in cells by *T. cruzi,* $10^5$ peritoneal exudate macrophages from IL-12yet40 reporter mice were incubated with $10^3$ *T. cruzi* trypomastigotes for 18 hours at 37° C./5% $CO_2$. The proportion of YFP$^+$ macrophages was determined by flow cytometry. LPS or media served as controls.

Determination of Caspase 1 Activity

Active caspases were detected with FLICA Apoptosis Detection kit (ImmunoChemistry Technologies, LLC, Bloomington, Minn.) following the manufacturer's protocol. After 12 hours incubation of $2\times10^4$ TcgFliC or Tcwt with $2\times10^5$ RAW blue (TLR 5) mouse macrophages (InvivoGen, San Diego, Calif.), the latter were incubated with a fluorescent inhibitor peptide specific to caspase 1 (FAMYVADFMK, SEQ ID NO:1) for 60 minutes at 37° C./5% $CO_2$. Inhibitors were removed by rinsing, the cells were fixed, and then the cells were analyzed with a florescence plate reader.

Intracellular Cytokine Staining for IL-1β, IFNγ and TNFα

To measure IL-1β production, $2\times10^5$ RAW blue (TLR 5) mouse macrophages (InvivoGen, San Diego, Calif.) were incubated with $2\times10^4$ TcgFliC trypomastigotes for 18 hours. *E. coli* lipopolysaccharide (LPS)+ATP or media served as controls. The induced IL-1β in macrophages were determined by staining using the CYTOFIX/CYTOPERM intracellular staining kit (BD Biosciences, San Jose, Calif.) following the manufacturer's protocol.

Similarly, to determine intracellular IFNγ and TNFα production, $1.5\times10^6$ spleen cells from TcgFliC-infected, TcgPorB-infected, or Tcwt-infected, or naïve mice were restimulated with *T. cruzi* peptide TSKb20 (5 μM) or *T. cruzi* whole cell lysate (10 μg) and processed for intracellular cytokine staining (ICS). The splenocytes were washed in PAB (2% BSA, 0.02% azide in PBS) and stained for surface expression of CD4, CD44, and CD8 using anti-CD4 PE, CD44 FITC, and anti-CD8 eFluor450 (BD Biosciences, San Jose, Calif.). All cells for ICS were fixed and permeabilized using CYTOFIX/CYTOPERM (BD Biosciences, San Jose, Calif.) on ice for 15 minutes and washed in PERM/WASH buffer (BD Biosciences, San Jose, Calif.). The cells were then stained with anti-IL-1β PE (R&D Systems, Inc., Minneapolis, Minn.), anti-IFNγ APC or anti-TNFα PECy7 (both BD Biosciences, San Jose, Calif.) for 30 minutes on ice. Cells were washed and fixed in 2% formaldehyde for 20 minutes at 4° C., then washed and resuspended in PAB for flow cytometric analysis.

Phenotyping Cells by Flow Cytometry T cell phenotypes were determined as described previously (Bustamante et al., 2008. *Nature Med* 14:542-550) and stained with tetramer-phycoerythrin (TSKb20-PE; NIH Tetramer Core Facility) and the following: anti-CD62L APC, anti-CD44 FITC, anti-CD8 efluor-450, anti-CD127 PEcy7 and anti-KLRG1 APCcy7 (all from eBioscience, Inc., San Diego, Calif.). Anti-CD4 PECy5 (Invitrogen, Life Technologies Corp., Grand Island, N.Y.) and anti-B220 PECy5 (Invitrogen, Life Technologies Corp., Grand Island, N.Y.) staining was used for a dump channel.

To determine the phenotypes of cells infiltrating the site of infection, the tissue (ear) was enzymatically digested to dissociate the cells as previously described (Phythian-Adams et al., 2010. *J Exp Med* 207:2089-2096). In the case of draining lymph nodes, the cells were dissociated by gently crushing between the ground edges of glass slides. After FcR (CD16/32) block, cell surface markers were used to differentiate several cell lineages as previously described (Phythian-Adams et al., 2010. *J Exp Med* 207:2089-2096). DCs, infiltrating monocytes, or resident macrophage subsets were differentiated using the following mAb conjugations: CD11c APC (eBioscience, Inc., San Diego, Calif.), CD8α efluor450 (eBioscience, Inc., San Diego, Calif.), CD11b APC/eFluor780 (BD Biosciences, San Jose, Calif.), Gr-1 (Ly6C/Ly6G) PerCP/Cy5.5 (BioLegend, San Diego, Calif.), F4/80 PECy7 (eBioscience, Inc., San Diego, Calif.) and CD45 PE (BD Biosciences, San Jose, Calif.). DCs were defined with CD11c, with further differentiation into $CD11b^-CD8\alpha^+$ cDCs and $CD11b^+$ $(F4/80^-)$ DCs. Monocytes and iDCs were defined as $CD11b^+$ $CD11c^-Gr\text{-}1^{int}$ and $CD11b^+$ $CD11c^+$ $Gr\text{-}1^{int}$ respectively as described (Turley et al., 2010. *Nat Rev Immunol* 10:813-825). Macrophages were identified as $F4/80^+$ $CD11b^+$ $CD11c^-$. IL-12 producing DCs were defined as $CD11c^+$ $CD8\alpha^+$ $(CD11b^-)$ $YFP^+$ in IL-12yet40 reporter mice as described before (Reinhardt et al., 2006. *J Immunol* 177:1618-1627). Data is represented as the percentage of each cell type over all the cells derived by enzymatic digestion, representing the total cellularity at the site.

IFNγ producing CD8 T cells in the draining lymph nodes of yeti mice were defined as $CD4^-B220^-CD8^+YFP^+$ as described (Mayer et al., 2005. *J Immunol* 174:7732-7739). At least $5\times10^5$ (blood) or $5\times10^6$ (peripheral tissue/lymph node) cells were acquired per sample using a CyAn™ flow cytometer (Beckman Coulter, Inc., Brea, Calif.) and analyzed with FlowJo software (Tree Star Inc., Ashland, Oreg.).

Temporary anchoring of PAMPs on *T. cruzi*

FSL-biotin GPI anchor with a single biotin F-moiety (FSL-CONJ(1Biotin)-5C2-L1, KODE Biotech Materials Ltd., Auckland, New Zealand) was used to coat *T. cruzi* trypomastigotes according to the manufacturer's protocol. $1\times10^6$ trypomastigotes were incubated with 2 μg of FSL-biotin in 100 μl serum free RPMI 1640 media. After washing to remove the excess FSL-biotin, the parasites were incubated on ice with streptavidin (Sigma-Aldrich, St. Louis, Mo.), at 5× the molar concentration of FSL-biotin (to give Tc-GPI). Excess streptavidin was removed by washing and various biotinylated ligands: FliC-biotin, Pam3CSK4-biotin (Pam3Cys-Ser-(Lys)4-biotin, InvivoGen, San Diego, Calif.), ODN-biotin (oligodeoxynucleotide-biotin, InvivoGen, San Diego, Calif.), all at 3× molar concentration of FSL-biotin or Pam3CSK4-biotin and ODN-biotin together, each at 1.5× molar concentration of FSL-biotin were incubated with the Tc-GPI for 30 minutes on ice to yield Tc-GPI-FliC, Tc-GPI-Pam3CSK4, Tc-GPI-ODN, or Tc-GPI-ODN-Pam3CSK4, respectively. FliC was biotinylated using EZ-link sulfo-NHS-LC Biotinylation kit (Thermo Fisher Scientific Inc., Rockford, Ill.) following the manufacturer's protocol. The various PAMP-anchored *T. cruzi* strains were washed twice with RPMI1640 to remove excess PAMPs, counted, re-suspended in complete RPMI1640 and used for in vitro or in vivo assays. Tc-GPI was used as the control. PAMPs when co-inoculated with *T. cruzi*, were used at approximately the same quantities (in w/v) as was used to label *T. cruzi* above.

Statistical Analysis

Data are presented as the mean plus/minus the standard error of mean. Statistical analyses compared the groups with a student t test. Only p values of less than 0.05 were considered statistically significant.

Western Blot and ELISA

To determine the presence of FliC, TcgFliC lysate was prepared as described (Martin and Tarleton, 2005. *J Immunol* 174:1594-1601). The lysate or culture supernatant (12 hours post-inoculation) were probed with anti-FliC mAb (BioLegend, San Diego, Calif.) by western blot, as described (Fralish and Tarleton, 2003. *Vaccine* 21:3070-3080). Sera collected from C57BL/6 mice infected with various *T. cruzi* strains, 30 days post-inoculation were assayed for anti-*T. cruzi* antibodies by ELISA as described (Gupta and Garg, 2010. *PLoS Negl Trop Dis* 4:e797).

To determine the relative concentrations of haemagglutinin (HA)-tagged protein (PAR4-HA) in the trypomastigote stage from various strains of transgenic *T. cruzi*, serial dilutions of whole cell lysates were assayed with anti-HA antibody (Roche). A purified HA-tagged protein (*T. cruzi* PAR2) expressed in *E. coli* was used as the standard.

Images were acquired with a DeltaVision™ Elite (Applied Precision, Issaquah, Wash.), were deconvolved and adjusted for contrast using its Softworx software v5.5 (Applied Precision, Issaquah, Wash.).

Serum Cytokine Assay

Blood collected from C57B1/6 mice inoculated with TcgFliC or Tcwt at four days post-inoculation and sera separated to assay for various cytokines using the Q-Plex™ Mouse Cytokine Screen ELISA (Quansys Biosciences, Logan, Utah) following the manufacturer's protocol. Luminescence intensity of each sample was measured and the concentration of each cytokine was determined using the Q-View™ software (Quansys Biosciences, Logan, Utah) as described (Kriegel and Amiji, 2011. *Clin Trans Gastroenterol* 2:e2).

Real-time PCR

The skeletal muscle tissue from mice were analyzed by real-time PCR for the presence of *T. cruzi* (DNA) as described before (Cummings, K. L. and Tarleton, R. L., 2003. *Mol Biochem Parasitol* 129:53-59.

Assessment of Infectivity and Clearance of *T. cruzi*

To assess the infectivity of different strains of *T. cruzi*, $IFN\gamma^{-/-}$ mice were inoculated with $10^4$ trypomastigotes of TcgFliC or Tcwt strains. Blood was collected from the tail vein at 21 days post-inoculation to quantify the number of parasites using a compound light microscope and expressed as the number of live trypomastigotes per 100 (40×) fields. Survival was monitored daily. Clearance of *T. cruzi* from infected mice were determined as previously described (Bustamante et al., 2008. *Nature Med* 14:542-550).

Determining *T. cruzi* Specific $CD8^+$ T Cell Response and their Phenotypes

The T cell phenotypes were determined as previously described (Kurup, S. P. and Tarleton, R. L., 2013. *Nature communications* 4:2616). In short, infected or naïve mice peripheral blood was collected by tail bleeding in Alsever's solution (Sigma-Aldrich, St. Louis, Mo.) and washed twice in staining buffer (2% BSA, 0.02% azide in PBS (PAB)). The blood was then incubated for 30 minutes at 4° C. in the dark with tetramer-phycoerythrin (PE) and the following antibodies: Allophycocyanin (APC) labeled antibody to CD62L, Fluorescein iso-thiocyanate (FITC)-labeled antibody to CD44, Allophycocyanin (APC)-Cy7labeled antibody to KLRG1, Phycoerythrin (PE) Cy5-labeled antibody to CD11c, CD4 and B220 for the exclusion channel (all from BD Biosciences, San Jose, Calif.), PE-Cy7 (eBioscience, Inc., San Diego, Calif.) labeled antibody for CD127 and eFluor450-labeled antibody to CD8 (eBioscience, Inc., San Diego, Calif.). The stained whole blood was then treated with hypotonic ammonium chloride solution to lyse red blood cells, and then washed twice in PAB and fixed using 2% formaldehyde. We acquired at least 500,000 cells with a CyAn™ flow cytometer (Beckman Coulter, Inc., Brea, Calif.) and analyzed with FlowJo software (Tree Star Inc., Ashland, Oreg.).

Major histocompatibility complex (MHC) class I tetramers were synthesized at the Tetramer Core Facility (Emory University, Atlanta, Ga.). The tetramer used in these studies was TSKb20/$K^b$ (ANYKFTLV, SEQ ID NO:2, on $H2K^b$).

The data are represented as percentage of TSKb20/$K^b$ tetramer specific $CD8^+$ T cells (% $TSKb20^+CD8^+$ T cells) over the total $CD8^+$ T cells (FIG. 16), or as the proportion of TSKb20/$K^b$ tetramer specific, or activated ($CD44^+$) $CD8^+$ T cells with the indicated phenotypes (FIGS. 13A, 14A, and 17), in circulation in the mice. To determine the fold increase in tetramer, the TSKB20/$K^b$ T cell response measured at each time point after TcgFliC or Tcwt re-challenge infection in chronically infected mice were divided by their corresponding levels at the time of re-challenge (FIG. 15).

Determining Tissue Loads of *T. cruzi*

Tissue loads of *T. cruzi* were determined as described. (Cummings, K. L. and Tarleton, R. L., 2003. *Mol Biochem Parasitol* 129:53-59). In brief, mouse skeletal muscle (300 mg) tissues were minced using surgical blades and added to 5× volume of sodium dodecyl sulfate-proteinase K lysis buffer containing 10 mM Tris-HCl (pH 7.6), 0.1 M NaCl, 10 mM EDTA, 0.5% sodium dodecyl sulfate and 300 μg of proteinase K/ml. The samples were then heated for 10 hours at 55° C. and extracted twice with phenol-chloroform-isoamyl alcohol. For quantification, reaction mixtures contained the extracted DNA, 0.5 μM primer mix, 10 μl of iQ™ SYBR Green PCR Master Mix (Bio-Rad Laboratories, Inc., Hercules, Calif.), and PCR-grade $H_2O$ (Qiagen Inc., Valencia, Calif.) to a final total volume of 20 μl. *T. cruzi* DNA and murine TNF-α DNA (as control for tissue DNA quantity) was amplified using an iCycler iQ™ real-time PCR system (Bio-Rad Laboratories, Inc., Hercules, Calif.). The primers used to amplify *T. cruzi* DNA were TCSat30: 5'-GGCGGATCGTTTTCGAG-3' (SEQ ID NO:3) and TCSat179: 5'-AAGCGGATAGTTCAGGG-3' (SEQ ID NO:4): The *T. cruzi* loads in the tissue was represented as DNA equivalents per 50 ng tissue DNA (FIG. 18).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising a transgenic *T. cruzi* that expresses a heterologous pathogen associated molecular pattern (PAMP) or a damage associated molecular patterns (DAMP).

2. The composition of claim 1 wherein the PAMP comprises an agonist of at least one Toll-Like Receptor (TLR).

3. The composition of claim 2 wherein the TLR comprises TLR 1, TLR 2, or TLR 5.

4. The composition of claim 1 wherein the PAMP comprises an agonist of at least one intracellular pattern recognition receptor (PRR).

5. The composition of claim 4 wherein the PRR comprises Neuronal Apoptosis Inhibitory Protein 5/IL-1β-converting enzyme protease-activating factor (NAIP5/Ipaf).

6. The composition of claim 1 wherein the transgenic *T. cruzi* is attenuated.

7. A method of treating an infection in a subject, the method comprising:

administering to the subject, in an amount effective to treat the infection, a *T. cruzi* genetically modified to express a pathogen-associated molecular pattern (PAMP).

8. The method of claim 7 wherein the *T. Cruzi* is attenuated.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: artificial
<220> FEATURE:
<223> OTHER INFORMATION: synthetic caspase 1 fluorescent inhibitor
      peptide

<400> SEQUENCE: 1

Phe Ala Met Tyr Val Ala Asp Phe Met Lys
1               5                   10


<210> SEQ ID NO 2
<211> LENGTH: 8
<212> TYPE: PRT
<213> ORGANISM: artificial
<220> FEATURE:
```

-continued

```
<223> OTHER INFORMATION: synthetic major histocompatibility complex
      (MHC) class I tetramer

<400> SEQUENCE: 2

Ala Asn Tyr Lys Phe Thr Leu Val
1               5


<210> SEQ ID NO 3
<211> LENGTH: 17
<212> TYPE: DNA
<213> ORGANISM: artificial
<220> FEATURE:
<223> OTHER INFORMATION: synthetic oligonucleotide primer

<400> SEQUENCE: 3

ggcggatcgt tttcgag                                                    17


<210> SEQ ID NO 4
<211> LENGTH: 17
<212> TYPE: DNA
<213> ORGANISM: artificial
<220> FEATURE:
<223> OTHER INFORMATION: synthetic oligonucleotide primer

<400> SEQUENCE: 4

aagcggatag ttcaggg                                                    17
```